(12) United States Patent
Blackburn et al.

(10) Patent No.: US 12,321,940 B2
(45) Date of Patent: *Jun. 3, 2025

(54) SYSTEM FOR VERIFICATION AND MANAGEMENT FOR DIGITALLY CASH TRANSACTIONS

(71) Applicant: Scientia Potentia Est., LLC, Charleston, SC (US)

(72) Inventors: Jeremy Blackburn, Charleston, SC (US); Justin Southward, Lehigh Acres, FL (US); W. Kurt Taylor, N. Charleston, SC (US); Karl David, Charleston, SC (US); Austi Critchfield, Clearwater, FL (US); Michael Lu, N. Charleston, SC (US); Tim McVicker, Charleston, SC (US)

(73) Assignee: Scientia Potentia Est., LLC, Charleston, SC (US)

( * ) Notice: Subject to any disclaimer, the term of this patent is extended or adjusted under 35 U.S.C. 154(b) by 476 days.

This patent is subject to a terminal disclaimer.

(21) Appl. No.: 17/566,957

(22) Filed: Dec. 31, 2021

(65) Prior Publication Data

US 2022/0198460 A1 Jun. 23, 2022

Related U.S. Application Data

(63) Continuation-in-part of application No. 17/561,827, filed on Dec. 24, 2021, now Pat. No. 11,574,319, (Continued)

(51) Int. Cl.
*G06Q 20/18* (2012.01)
*G06Q 20/40* (2012.01)
*G06Q 20/20* (2012.01)

(52) U.S. Cl.
CPC ....... *G06Q 20/40145* (2013.01); *G06Q 20/18* (2013.01)

(58) Field of Classification Search
CPC .......... G06Q 30/0185; G06Q 20/1235; G06Q 20/40145; G06Q 20/4015; G06Q 40/08;
(Continued)

(56) References Cited

U.S. PATENT DOCUMENTS

| | | | |
|---|---|---|---|
| 10,338,913 B2* | 7/2019 | Franchitti | H04L 67/34 |
| 2013/0092700 A1* | 4/2013 | Braunstein | G07F 9/001 |
| | | | 221/13 |

(Continued)

*Primary Examiner* — Garcia Ade
(74) *Attorney, Agent, or Firm* — Kim and Lahey Law Firm, LLC; Douglas W. Kim

(57) ABSTRACT

A computerized system for verifiably pairing financial events including a loan with a digital representation and a check cashing transaction with a digital representation comprising: a kiosk and controller in communication with a persistent storage; a sensor assembly in communications with the controller wherein the sensor assembly is adapted for sensing a borrower application as the loan origination location; a set of non-transitory computer readable instructions included in controller adapted for: determining the location of the kiosk, retrieving, from the persistent storage, a loan record representing loan from a lender to a borrower, creating a payment record including payment information captured by the sensor assembly representing a payment according to the loan record from the borrower wherein the payment record includes the date, time, payor, amount, location and any combination, associating the payment record with the loan record and storing the payment record on the persistent storage.

26 Claims, 27 Drawing Sheets

Related U.S. Application Data which is a continuation-in-part of application No. 17/531,746, filed on Nov. 20, 2021, now Pat. No. 11,482,325, which is a continuation-in-part of application No. 17/531,598, filed on Nov. 19, 2021, now abandoned, which is a continuation-in-part of application No. 17/344,043, filed on Jun. 10, 2021, now abandoned, which is a continuation-in-part of application No. 17/230,911, filed on Apr. 14, 2021, now Pat. No. 11,288,761, which is a continuation-in-part of application No. 17/176,056, filed on Feb. 15, 2021, now Pat. No. 11,288,308, which is a continuation-in-part of application No. 17/128,084, filed on Dec. 19, 2020, now Pat. No. 11,521,157, which is a continuation-in-part of application No. 16/997,840, filed on Aug. 19, 2020, now Pat. No. 11,449,949, which is a continuation-in-part of application No. 16/994,585, filed on Aug. 15, 2020, now Pat. No. 11,232,652, which is a continuation-in-part of application No. 16/991,916, filed on Aug. 12, 2020, now Pat. No. 11,216,823, which is a continuation-in-part of application No. 16/876,080, filed on May 17, 2020, now Pat. No. 11,423,360, which is a continuation-in-part of application No. 16/810,782, filed on Mar. 5, 2020, now Pat. No. 11,216,781, which is a continuation-in-part of application No. 16/510,634, filed on Jul. 12, 2019, now Pat. No. 10,713,737, and a continuation-in-part of application No. 16/510,642, filed on Jul. 12, 2019, now Pat. No. 11,216,772, said application No. 16/510,634 is a continuation-in-part of application No. 16/452,076, filed on Jun. 25, 2019, now abandoned, said application No. 16/510,642 is a continuation-in-part of application No. 16/452,076, filed on Jun. 25, 2019, now abandoned.

(58) Field of Classification Search
CPC ........ G06Q 20/18; G06Q 40/03; G16H 20/10; G16H 40/20; G16H 40/63; G16H 40/67; G16H 10/60
USPC .............................................................. 705/2
See application file for complete search history.

(56) References Cited

U.S. PATENT DOCUMENTS

| | | | |
|---|---|---|---|
| 2017/0031676 A1* | 2/2017 | Cecchetti | G06F 8/65 |
| 2019/0012637 A1* | 1/2019 | Gillen | G06Q 10/0833 |
| 2019/0279204 A1* | 9/2019 | Norton | G06Q 10/08 |

* cited by examiner

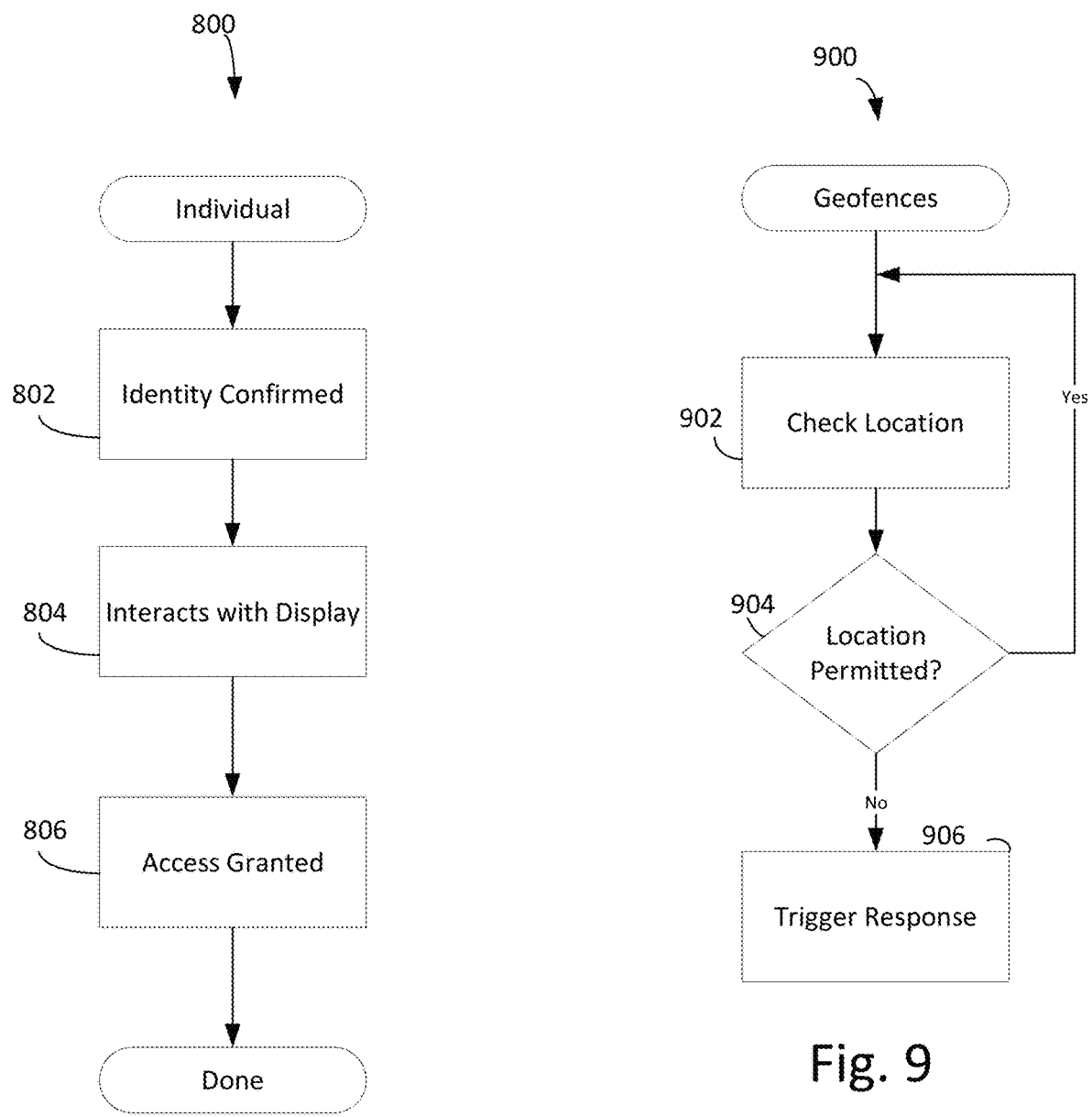

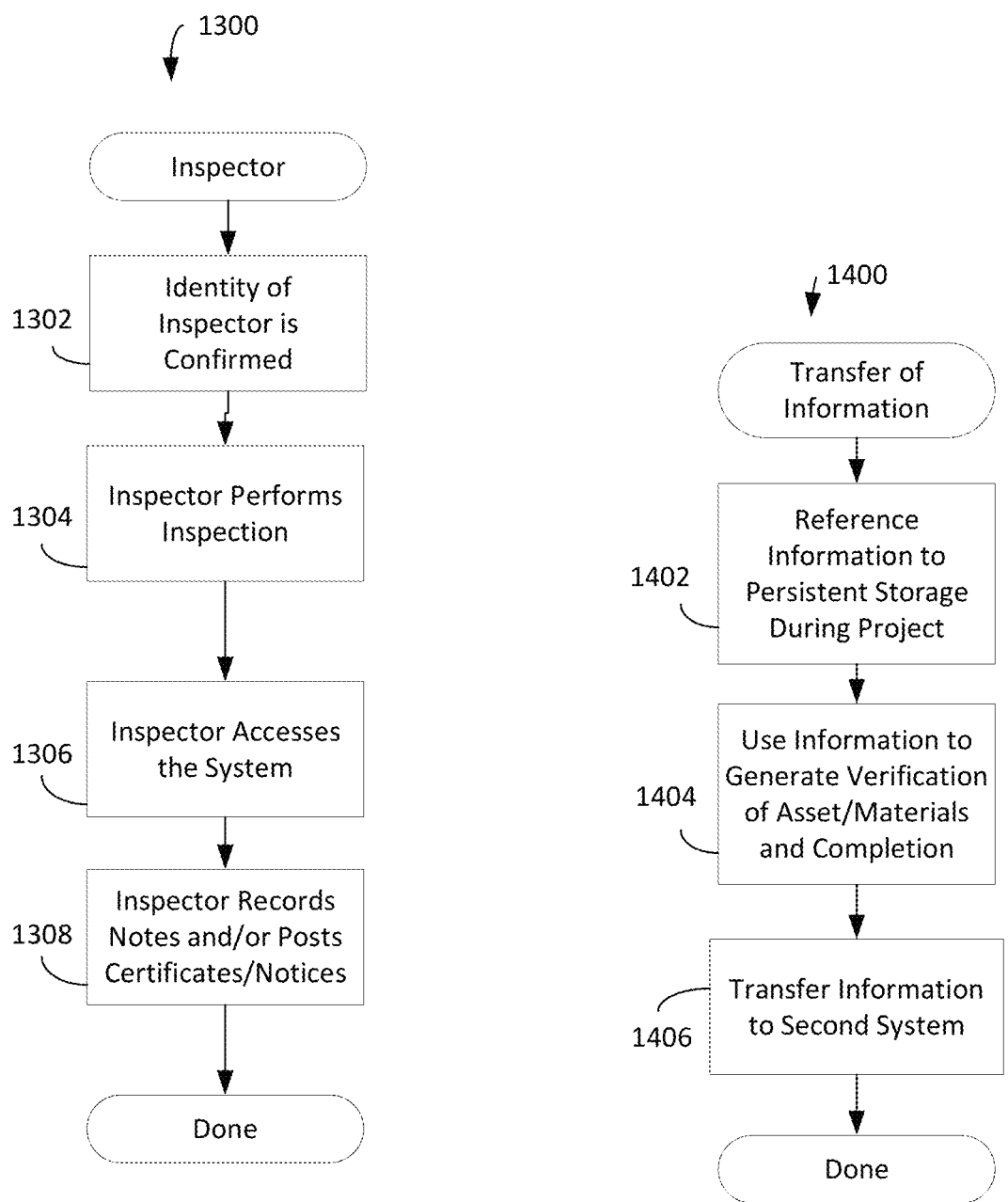

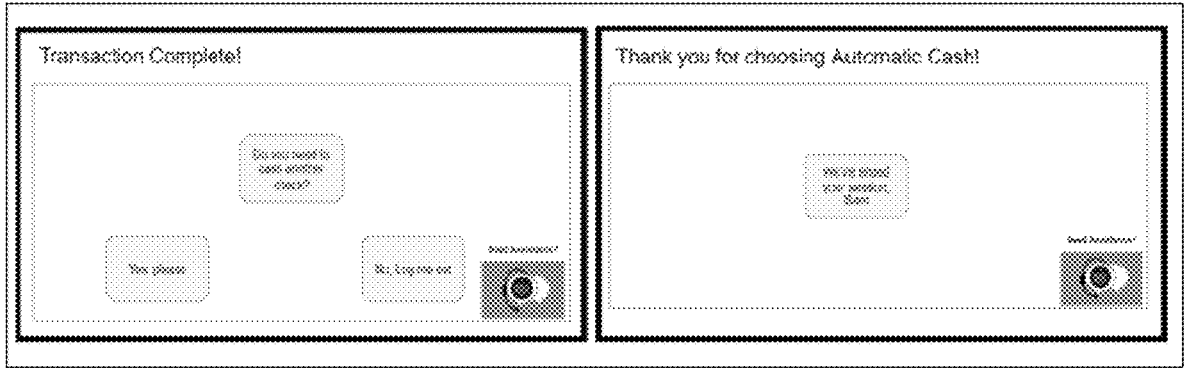
FIG. 18K
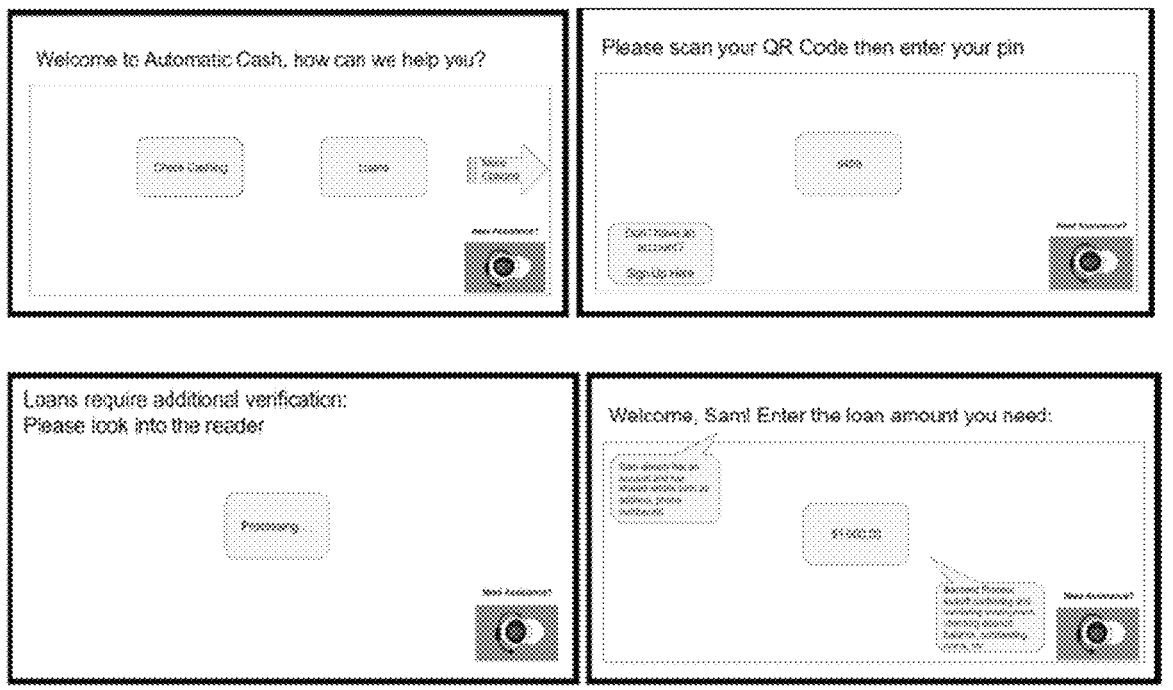
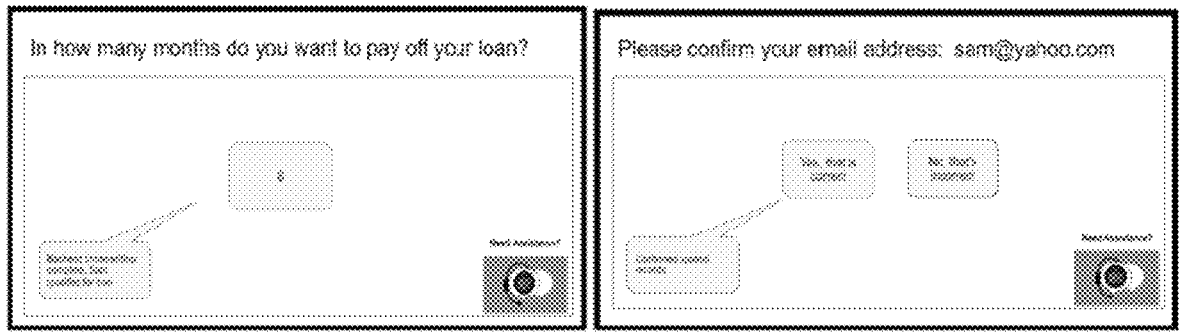
FIG. 18L

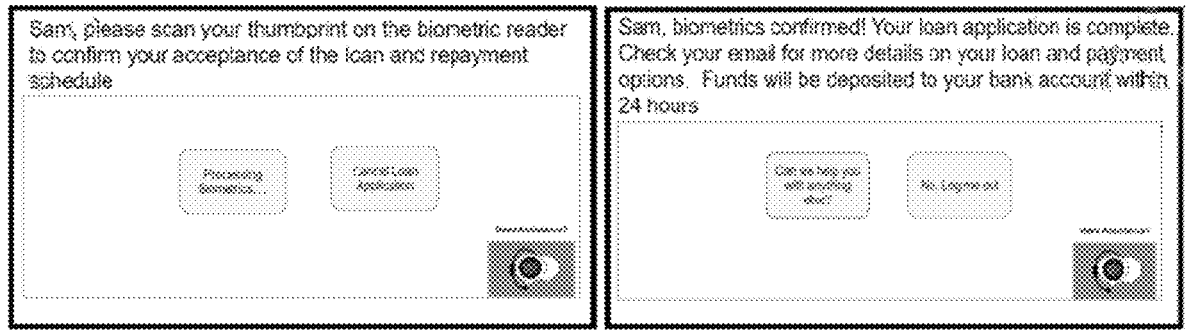
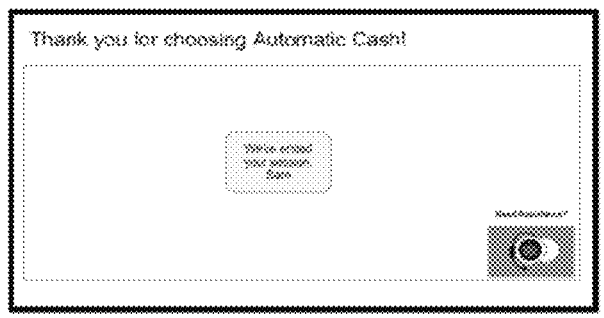
FIG. 18P
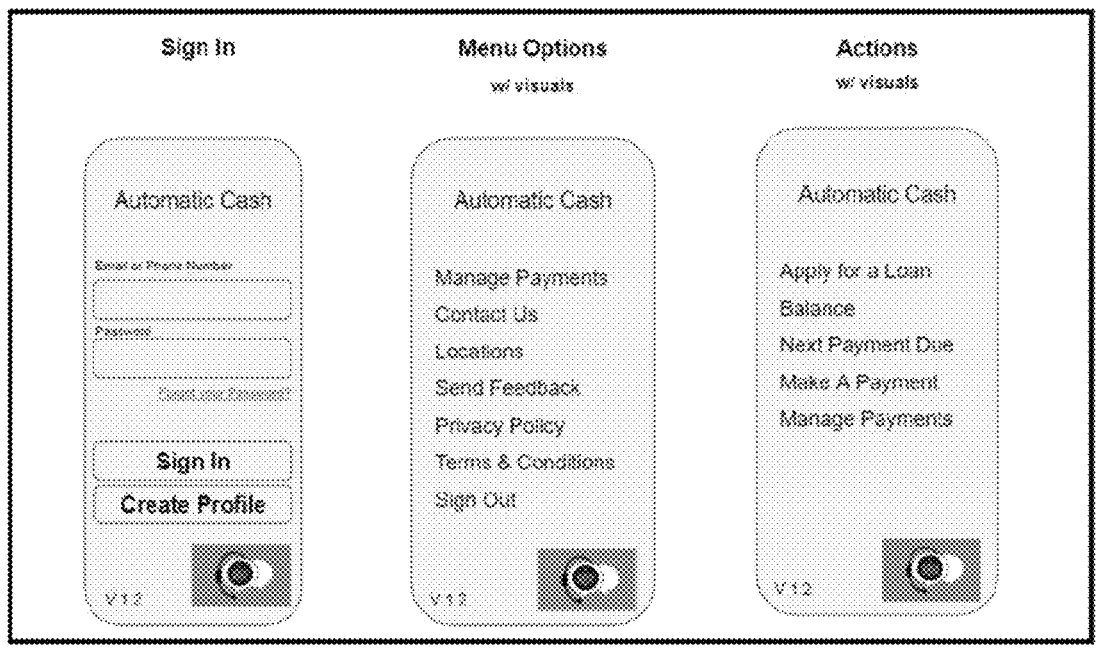
FIG. 18Q

SYSTEM FOR VERIFICATION AND MANAGEMENT FOR DIGITALLY CASH TRANSACTIONS

RELATED APPLICATIONS

This application is a continuation in part of U.S. patent application Ser. No. 17/561,827 filed Dec. 24, 2021 which is in turn a continuation in part of U.S. application Ser. No. 17/531,746 filed Nov. 20, 2021 which is in turn a continuation in part of U.S. application Ser. No. 17/531,598 filed Nov. 19, 2021 which in turn is a continuation in part of U.S. application Ser. No. 17/344,043 filed Jun. 10, 2021 which in turn is a continuation in part of U.S. application Ser. No. 17/230,911 filed Apr. 14, 2021 which in turn is a continuation in part of U.S. application Ser. No. 17/176,056 filed Feb. 15, 2021 which in turn is a continuation in part of U.S. application Ser. No. 17/128,084 filed Dec. 19, 2020 which in turn is a continuation in part of U.S. application Ser. No. 16/997,840 filed Aug. 19, 2020, which is a continuation in part of U.S. application Ser. No. 16/994,585 filed Aug. 15, 2020 which in turn is a continuation in part of U.S. patent application Ser. No. 16/991,916 filed on Aug. 12, 2020 which in turn is a continuation in part of U.S. patent application Ser. No. 16/876,080 filed May 17, 2020 which in turn is a continuation in part of U.S. patent application Ser. No. 16/810,782 filed on Mar. 5, 2020 which in turn is a continuation in part of U.S. patent application Ser. No. 16/510,634 filed on Jul. 12, 2019 (now U.S. Pat. No. 10,713,737 issued Jul. 14, 2020) and U.S. patent application Ser. No. 16/510,642 filed on Jul. 12, 2019, which are all incorporated by reference. patent application Ser. Nos. 16/510,542 and 16/510,634 are both continuations of U.S. patent application Ser. No. 16/452,076 filed Jun. 25, 2019, which all are incorporated by reference.

BACKGROUND

1) Field of The Invention

A system for approving, processing, and pairing a check cashing system and loan processing system verifiably link a digital representation of the individual and the transaction, including any collateral and associated transactions with a verifiable digital representation. This system can create an undichotomized pairing that can be used for approval, generation, authentication, verification, anti-counterfeit, appraisals, auditing, recording and the like. The system can provide for a verified digital record of check cashing, loan status, loan activity, and related transactions.

2) Background

There has been a significant increase in the number of individuals that need to cash checks or borrow funds where the individual is either are unbanked or wishes not to use a bank. In the event that the individual does not have a banking relationship, check cashing services provide the ability to receive fiat currency without having to deposit a check into an account. Typically, an individual with a paycheck or government check is presented to a check cashing service, the cashing service will verify identity, cash the check, and dispense money immediately, minus a fee. This is in contract to depositing the check into a bank or credit union account where there can be a delay of days waiting the check to clear. Proper identification of the individual, assurance that funds where the check is drawn are available and a check cashing history with the service are issues that are not readily addressed in the industry.

Individuals also may seek short-term loans that are typically of a small dollar amount and can be unsecured loans (e.g., used to manage cash flow between paychecks or other regular income payments) or secured (e.g., title loans). These loans are usually needed by borrowers for unforeseen expenses and require quick access to cash.

One such loan is a payday loan that is short-term and provides for generally immediate cash needs prior to a subsequent paycheck. These loans are usually high-cost loans and can include triple-digit annual percentage rates (APRs). Payments are usually in the short term such as being due within one or two weeks, or as close to the subsequent paycheck as possible. While offering utility to the borrower, these loans have increased risks to the lender as the loan can be difficult to repay. According to the Consumer Federation of America ("CFPB"), payday loan APRs are usually 400% or more. Regardless of the high interest rates, The Economist estimates that 2.5 million American households take out payday loans each year. It is reported that these loans tend to be requested by those without other financing options due to poor credit, no income or no financial history. Traditionally, these loans have a higher risk than traditional lending. The CFPB found that 20% of payday borrowers default and more than 80% of payday loans taken out by borrowers were rolled over or reborrowed within 30 days. It would be advantageous to have a system that allowed for these short-term loans while also considering the payment history (e.g., credit worthiness) of the borrower to allow for lower interested rates once the payment history of the borrower is established.

Another method of securing generally immediate cash liquidity is by using title loans. Title loans can be desirable for a borrower because the loan is based upon exchanging a car title as collateral and does not necessarily depend upon a credit score. Due to the nature of the loans, the average APR can be 300%. While title loans are typically thirty days, the monthly rate can be 25%. Further, many borrowers roll the loan into the second month which results in an additional 25% monthly interest rate. As with payday loans, the CFPB found that 80% of title loans rolled to the next month as well. The title loan has an additional factor in that if the loan is not repaid, the lender is allowed to repossess the vehicle, which the CFPB reports occurs 20% of the time. If would be advantageous to have a system that provided for title loans which consider the repayment history of the borrower and can adjust the interest rate downward according to payment history. This advantage would assist lenders and borrowers including those that are unbanked.

An explanation of these loans can be found in International Patent Application Publication WO2014052416. There have been attempts to improve these loans such as shown in U.S. Pat. No. 7,386,507 which discloses a system that permits a lender to offer short-term, small cash loans to employees through an employer-controlled payroll system. However, this system requires a pre-established relationship between a coordinator, a lender, and the employer. U.S. Pat. No. 9,607,236 is directed to loan verification from an image. This patent discloses using an optical image of a license plate and mobile apparatus and includes a license plate detector configured to process the electrical signal to recover information from the vehicle license plate image. However, this system is directed to loan qualifications and verification based upon third party data. This system does not provide for the ability to determine or adjust interest rates or loan terms based upon historical data of the unbanked borrower.

The disadvantages of current systems are caused in part due to the lack of pairing the lender, borrower, and loan with a virtual representation to determine that the parties involved, and the loan activity are properly physically and digitally paired.

There is also a need to verify that the individuals during the creation, authentication and loan are who they say that they are.

There is also a need to verify that the loan activity follows applicable standards, regulations and other requirements including the creation of an audit trail for the associated activity and transactions.

It would be advantageous to have a system that automatically, approves, processes, grants and verifies loans and the parties as well as loan activities. The verification should include date, time, location, individual, entity and other aspects of the loan and its processes to provide a verified virtual representation. It would be advantageous to have a system that reduces or eliminates the risk of default, advantageous assigns interest rates, reduces counterfeit, fraud, or and negative effects and combination of these.

Another disadvantage of the current loan processing system is that the data resulting from the authentications and verifications is not easily accessible by all stakeholders. For example, when a lender wishes to provide a loan to a borrower, unless that lender has prior experience with the borrower, the lender can only rely upon data from third parties (e.g., FICO scores). There has been some attempt to provide for improved "trustworthiness" through location—based verification with social networking such as disclosed in U.S. Pat. No. 10,255,602, but such attempts do not provide for a system that verified the parties and the loan activities including capturing date, time, location, and biometrics of the parties.

It would be an advantage to have a system that provide for approval, processing, granting, disbursement, transaction, collateral, and other activities and material associated with loans by using a verified virtual representation.

It would be an advantage to have a system that can pair parties and loans with virtual representation so that verification and loan terms can be modified according to past transactions.

It would be advantageous to have a system that provides for a verified trustworthy association between physical material and virtual representations that is stored on an immutable or persistent ledger.

SUMMARY OF THE SYSTEM

In accordance with an exemplary embodiment, this system can include a computerized system for verification and management of transactions comprising: a kiosk having a controller disposed at a transaction origination location and in communication with a storage system. The transaction location can be at the kiosk where the user request that a check be cashed or where a loan request is made. The kiosk can be fixed at a permanent location or can be mobile. However, the user location and the transaction request location are recorded when the transaction request is made. The system can include a sensor assembly in communications with the controller wherein the sensor assembly is adapted for sensing a user identification information, a transaction request, and a transaction location. The transaction request can be taken from the group consisting of check cashing, loan or both. The system can include a set of computer readable instructions included in the controller or accessible by the controller that can be adapted for receiving the user identification information wherein the user identification can include a user location, an identification date and an identification time and the user identification information can be taken from the group consisting of a user image, a user facial attribute, a voice information, a retinal scan, a fingerprint, a venous pattern, a gait information, a handprint, and any combination thereof. The sensor can be a camera or other image capture device, facial recognition, voice recognition, retinal scans, fingerprint scanners, hand scanners, other biometric devices, weather sensors, light sensors, accelerometers, or pressure sensors. The system can be adapted for receiving the transaction request wherein the transaction request includes a transaction request date and a transaction request time. The transaction request can be a request to cash a physical check, request to cash an electronic check, or a loan request.

The system can be adapted for can determining the transaction origination location, determining a kiosk location, and retrieving an approval criterion from a computer readable medium in communications with the controller. The approval criterion can include receiving a sufficient funds notification from the check issuing bank that there are sufficient funds in the account associated with the check so that the risk of cashing the check is reduced. The approval criterion can be the loan payment history of the individual. For example, the system record and store past loan request, loan approvals, loan disbursements and repayments. As the user builds a history of timely payments, the risk of the loan to that user can be reduced and the loan more readily approved. The approval criterion can include the location of the kiosk or the loan request. For example, payday loans are not legal in all states so that the system can allow for disabling of certain transaction in certain geographic locations. The approval criterion can include transaction details such as a minimum or maximum interest rate, amount of quantity of loan for an individual. For example, certain geographic locations do not allow interest rates above a certain value and certain geographic location limit associated transaction fees. Others limit the number of loans of a certain a borrower can make. In one state, a borrower may only receive a certain number of payday loans a year. If a transaction request exceeds these approval criteria, the transaction can be denied. Approval criterion can include the payment history of the user wherein the more positive the payment (e.g., repayment history) the lower to risk of approving the transaction. The system can compare the approval criterion with the user identification information and the transaction request and determine if the transaction should be allowed.

The system can be adapted for initiating a transaction approval wherein the transaction approval includes an approval location, an approval date, and an approval time. This information can be collected and stored for purposes that include regulatory compliance, history of the user and the like. The approval process can include comparing the user identification information and transaction request with the approval criterion and if they are consistent, the transaction can be approved. The transaction location, kiosk location and user location information can be collected and compared so that if they are consistent, the transaction can be approved. In one example, the system can retrieve the physical address of the payor of a check with the kiosk location. If the address and location are not in the same predetermined vicinity (e.g., state) then the check cashing result may be denied. The system can determine the identification date, the identification time, the request date, and request time and compare these to determine if they are consistent. For example, if the identification date and time and the requits date and time are too far apart, the transaction can be denied.

The information captured can be stored on the storage system. The storage system can be a persistent storage, distributed ledger, a first database and a second database and any combination. The information captured can include a token that is associated with a record and stored on blockchain types recording system the record data can be stored on a second database. The second date base can be immutable and distributed.

The system can be adapted for initiating transfer of funds from a first account to a second account according to the transaction approval. The system can automate this using the transaction approval and preexisting self-executing actions. Conditions associated with the transaction can be created and when the conditions are met, the system can act. For example, if a loan includes a UCC-1 filing, the system can automatically generate the UCC-1 and have it transmitted to the proper authority. When the loan is repaid, the UCC-1 can be deemed satisfied and automatically be transmitted to the authority. If collateral is involved, the system can automatically place a lien on a chain of title and record the lien at the proper authority. When the loan is paid, the lien can be satisfied. The system can automatically encumber the title of collateral such as transmitting the encumbrance to the property authority, store the encumbrance on the storage system or other notifications that title to the property is not clear.

The system can be adapted for receiving a payment information representing a payment into the first account from the user and reducing a balanced due associated with the second account. The system can have a receiver included in the kiosk adapted for receiving a physical payment and wherein the computer readable instructions are adapted for associating the payment information with the transaction approval. The received can also receive a check to be cashed, title to collateral or other physical information. The received can record collateral identification information (e.g., a vehicle VIN) and store is on the storage system. In the embodiment, the activity associated with the vehicle can be recorded so that any lien or other encumbrance on the vehicle title can be stored and retrieved. The system can be adapted for recording the payment on the storage system and associating the payment information with the transaction approval.

The kiosk can include a note dispensing assembly and a slot defined in the kiosk and wherein the computer readable instructions are adapted for dispensing a note (e.g., cash, pre-paid card, commercial paper, or other cash equivalent) according to the transaction approval. The system can be adapted for initiating a transaction approval upon comparison of the user identification information with a user history information. The system can be adapted for calculating a chain value according to the transaction approval and an interest rate according to the chain value. A chain value can be a set of interest rates that chance with payments. When the borrower makes the first payment the interest rate can be A. When the borrower makes the Xth payment, the interest rate can be reduced to B. As the borrower makes payments the interest rate can be reduced. One example is shown in Table 1 below:

TABLE 1

| Payment No | Interest |
|---|---|
| 1 | A |
| 2 | A |
| 3 | A |
| 4 | A − x |

TABLE 1-continued

| Payment No | Interest |
|---|---|
| 5 | A − x |
| 6 | A − x |
| 7 | A − y | where A is the initial interest rate, x is a positive number and y>x.

The system can be adapted for receiving an income information from a third party and initiating the transaction approval according to the income information. The income information can be from the borrower's employer of other source. If the borrower has a sufficient income, the transaction can be approved, and the interest rate can be determined to be lower than an insufficient income level. The system can be adapted for receiving a history information and initiating the transaction approval according to the history information. The transaction request can include a check information, and the computer readable instructions are adapted for initiating the transaction approval when the check information includes an existing account. The transaction request can include a collateral information, and the computer readable instructions are adapted for initiating the transaction according to the collateral information. The collateral information can include title to the collateral or an image of the collateral. In the event that the collateral is the title to property, the title (e.g., document) can be received by the kiosk and held until a loan is satisfied. The system can place a notation on the title reflecting the loan, lien or encumbrance associated with the title. The system includes a documents receipt assembly and the system can be adapted for receiving an ownership information associated with the collateral information. The system can determine when a payment is a final payment, and the computer readable instructions can be adapted for creating a satisfaction information representing that a loan associated with the transaction approval have been satisfied. The system can return the title documents, release any lien, record the loan satisfaction on the storage system, update a UCC filing and other action.

The system can be adapted for receiving collateral information associated with the transaction approval, capturing collateral identifying information with the sensor assembly, creating a collateral record according to the collateral information and associating the collateral information with the transaction approval. The system can automatically encumber a title associated with the collateral. The system can record an encumbrance against the title associated with the collateral. The encumbrance associated with the collateral information can be stored.

The system can be adapted for creating a risk record associated with the user including a set of transaction approvals associated with the user. The risk record can include a risk value wherein the risk value is adapted for reduction according to the set of transaction approvals. The risk record can include an interest rate wherein the interest rate is adapted for reduction according to the set of transaction approvals. For example, the risk and therefore interested rate can be reduced when the borrower takes out and satisfies previous loans. The user identification information can be stored immutably on a computer readable medium in communications with the controller.

BRIEF DESCRIPTION OF THE DRAWINGS

FIGS. 8-9 shows a flowchart illustrating aspects of the system.

FIGS. 11-16 show flowcharts is aspects of the system.

DETAILED DESCRIPTION

Figure 1A:
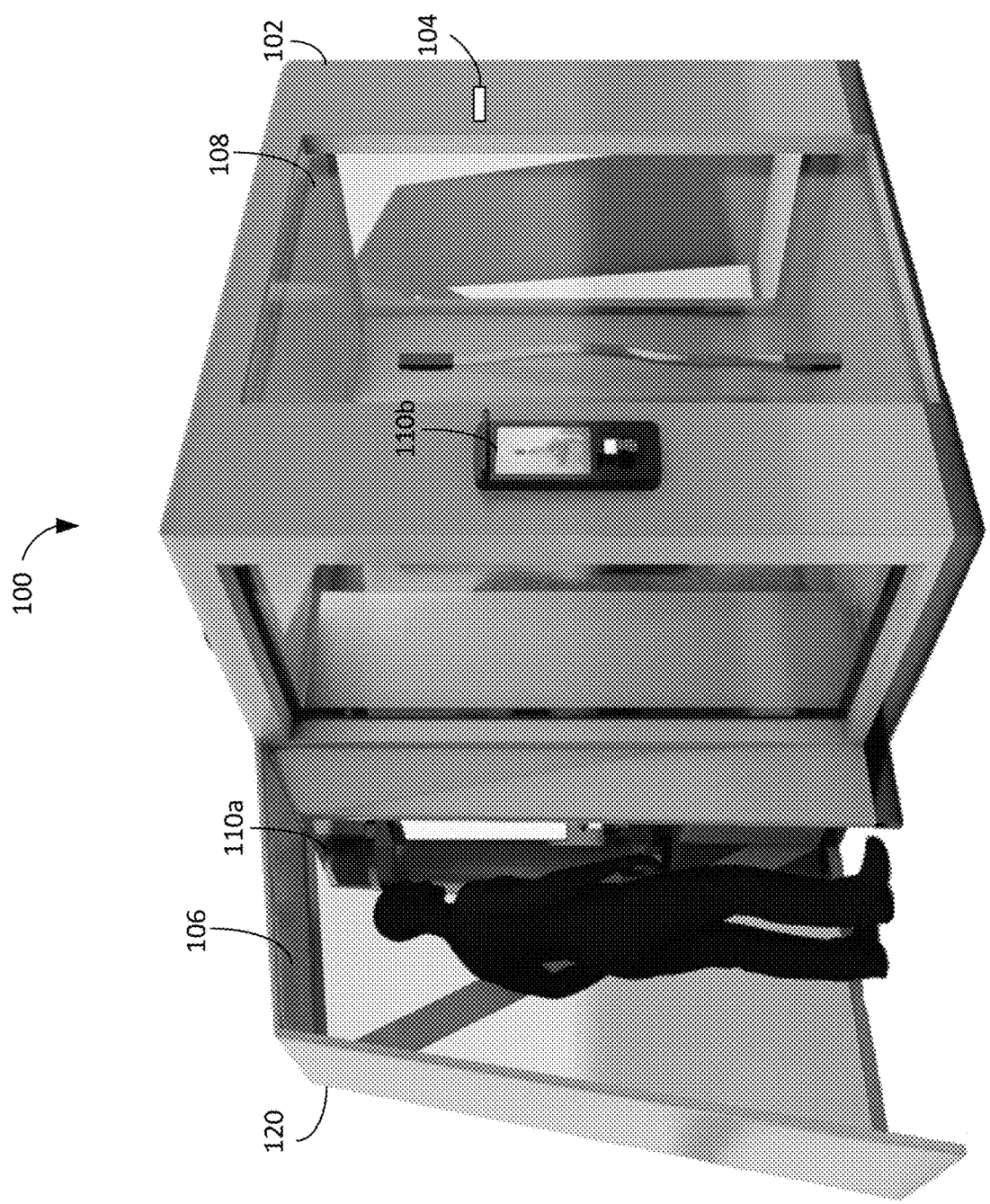
FIGS. 1A and 1B are perspective views of aspects of the system.

The present system provides for real time verified pairing of a borrower with a loan so that the borrower and the loan are verifiable paired with a virtual representation. The system provides for the approval, preparation, granting, payments and satisfaction of the loan without the borrowers needing a preexisting bank account. The server or kiosk can include a set of server computer readable instructions configured to receive information about the lender, borrower, and loan that can include the ability to capture information such as the description of collateral, transactions, financial information, characteristics of the parties and loan, employment, income, debt, credit information, and the like.

The system can capture information that includes one or more unique identifiers uniquely associated with the lender, borrower, loan, transaction, collateral, and the like. An inspector, individual or automated, can visually inspect the information, collateral or other material and verify that the borrower was at a location where the loan was requested, a transaction occurred of collateral was provided. The system can retrieve financial and employment information used for the loan application, processing, transactions and satisfaction and verify that the borrower, and inspector, was present and the loan activity occurred at the stated date, time, and location. Images of inspector, borrower, lender, and transaction can be compared with environmental information (e.g., weather) at the location, date, and time. In one embodiment, the background of an image showing the environmental conditions can be compared with third party weather information for verification that a record reflecting the loan activity matches the existing environmental conditions. For example, if the image of the loan activity shows a cloudy day (e.g., in the background) and third-party weather information confirms a cloudy day, the confidence of the virtual representations of the loan activity increases. Biometric data can be captured from a party as well as attendance information from an access control system to verify that a party was at a use location at the date and time a record or other virtual representation is created. A loan activity record may be created or updated as a loan is created and have serial numbers, bar codes, QR codes, RFID values, beacons, lots, microdots, sizes, or other marking, identifiers or material added or associated with the loan in physical form. The persistent storage can be disposed at the location of the loan, lender, or borrower or can be remote from such location. The system can also provide the material record to a third-party such as a financial institution, employer service provider (e.g., repossession company) that can assist with loan transactions. The third party can review the loan record and determine if the loan specified is valid, current, or what action should be taken.

The loan record can include data and information representing the location, date, time, party and other information associated with a loan activity. A loan activity can be a loan request, application, approval, disbursement, payment, satisfaction and closing of a loan.

The system can identify individuals entering or leaving a location and store this information on the persistent storage. The verification can be through biometric identification devices such as a camera or other image capture device, facial recognition, voice recognition, retinal scans, fingerprint scanners, hand scanners, and other biometric devices. In one embodiment, the system includes computing logic that allows authorized individuals to manually enter the presence of another authorized individual, including on the kiosk or controller at the use location or through a remote device that can be determined to be at the use location, within a boundary associated with the use location, in proximity to the kiosk, controller or system. In one embodiment, individuals may be verified and paired with a virtual representation using two-factor authentication.

The individual can be provided with loan requirements or other requirements that can be represented by a loan requirement record. The loan requirement record can be stored on the persistent storage. In the event of collateral, the system can verify that the collateral is present (which can be individually inspected) according to the loan requirement record or loan record, create a collateral record and store the collateral record on the persistent storage. The collateral record represents that a physical item was properly received and verified. The loan record can include information that represents that the collateral was performed by proper individual and in compliance with any requirements as well as if the collateral passes one or more inspections. The loan record can include information that represents that a loan task was performed by proper individual and in compliance with any requirements.

Prior to, during, and after a loan is created, an inspection can be performed that can include a pre-loan inspection, loan inspection, post loan inspection and any combination. A pre-loan inspection, loan inspection, and post loan inspection record can be created so that these records can be stored on the persistent storage. The loan record can include information that the inspection resulted in passing, passing with deficiencies, and failing. If the inspection fails, the borrower, lender or other entities can be given the opportunity to remedy the failure and the inspection process can be performed again. The process can also determine if, while the loan passed the inspection, the deficiencies should be remedied.

The system can be uniquely associated with the use location such as a loan facility. A location marker can be affixed to the use location and uniquely identify the use location. The use location can be where the loan is generated, collateral is inspected, payments are made and the like. The location marker can be read by the system so that the system can determine its location. Third parties can access the location marker to verify that the third party is at the use location. Such access can be through hardware communications which as LTE, 5G, Bluetooth, WiFi and other wired and wireless communications. Information can be captured form personal devices of individuals including device ID number, date, time, locations, and the like. Such device information can assist with a determination of when and where an individual was at a time of an event or transaction.

The system can be contained in a housing such as a kiosk and can be physically associated with the use location. The use location can be defined by a boundary representing the perimeter of the use location. The system can include a sensor and reader which can be selected from the group consisting of radio frequency identification (RFID) detector, ultra-high frequency (UHF) detector, a bar code scanner, a QR code scanner, near frequency communication (NFC) device; Bluetooth beacons, an optical character recognition (OCR) device and any combination thereof. An environmental sensor, such as a weather sensor or weather station, can be in communications with the or included in the housing and configured to record the weather and other environmental conditions at the use location and at different times during the project. This information can be used to verify the authenticity of the parties, loan, and collateral.

The system may record the date and time of events such as loan approval, loan issuance, distributions, payments, closure, and the like. It can capture individuals to and from the use location as well as the date and time associated with these events as well as environmental conditions including weather. Recording environmental information, including weather, at the use location allows for autonomous confirmation of environmental conditions that do not rely solely on third party sources or sources that are general or distant from the use location. For example, if a record is associated with a particular party the environmental condition of that event can be recorded so that subsequent authentication can match the purported event location, date and time and weather conditions at that location, date and time to determine if there is a match.

The system may also determine if an unidentified individual attempts to enter the use location, the system may take the appropriate responses, such as sending notifications, triggering alarms, and/or contacting law enforcement authorities or security. The decision as to the appropriate response may be determined by, the date, the time, current weather conditions, authorizations, project or process status, or related factors. This functionality of the system can prevent the loss of material such as a jersey, game ball or other article from being taken without authorization.

The smart locks may also be used to limit access to certain portions of the use location. An individual's right to a specific collateral or funds may be dictated by permissions that are stored through each party involved in the process. This may eliminate keyed entry during the process and provide further verifications of individual or group access. For example, if fiat currency is provided to a storage area, access can be limited so that on one but authorized individuals (e.g., lender or their agents) are allowed to enter the storage area.

The individuals on the use location may be prompted to wear certain wearables that provide useful information to the system. For instance, individuals may be prompted to wear location tracking devices, such as GPS devices, Bluetooth, radio frequency identification (RFID) devices, ultra-high frequency (UHF) and/or beacon-based devices. The individuals can also be identified with portable device such as smart phones and when entering an area, provided on an app for an authentication. This allows the use of personal computer devices while also reducing or eliminated fraud or mistakes that can occur with unauthorized access to a personal computer device.

The use of the wearables helps to perform geofencing within the use location. The location tracking provided by the wearable helps the system to monitor the location of individuals on the use location on an ongoing basis. The permissions may define what portions of the use location an individual may access. Ongoing monitoring may indicate that an individual is attempting to enter a location where the individual is not permitted. This may trigger a response as described herein. A signal may be sent to the vest or wearable to trigger a visual or audio cue that the individual is not in a permitted area.

The system may track the movement of material such as collateral, cash, validation cards, identification cards, and other items at the use location or to and from the use location. Scanning technology such as RFID readers, UHF readers and/or the like may be utilized to assist the location tracking of material and even individuals. The tracking of material helps reduce the risk of loss, theft, mis-delivery, and the like. For example, the tracking solution may indicate instances of possible theft, such as when material is leaving the use location when the removal of the material is not proper.

The system may allow for the establishment of one or more geofenced zone that can be associated with use location and location of the material. These locations can include entrance areas, exit areas, event areas, storage areas, and any combination thereof. These areas could be monitored and established with access allowances or restrictions to control movement of materials, individuals, and equipment to assist with the prevention of loss, mistakes, fraud, theft, inefficiencies, and damage. The system can assist with verification that material stored at these locations are consistent with the information concerning the material status, locations, state, etc.

The system may also interface with individuals to allow for the entry of notes and related details of a loan or material, disbursement, payment, inspection, environmental condition individual, tasks, processes, or individual or any combination thereof. For example, the system may allow an inspector to capture images of notes, forms, documents, labels, and the like using various readers, sensors, and input devices. The system can capture the disbursement of funds, payments, and collateral Smart contracts may be provided that use the persistent storage for each event of the loan including approval, transferred ownership of collateral, placing a lien on collateral, disbursing funds, receiving payments, satisfaction of the loan, extending the loan, rolling the loan and any combination.

Figure 1B:
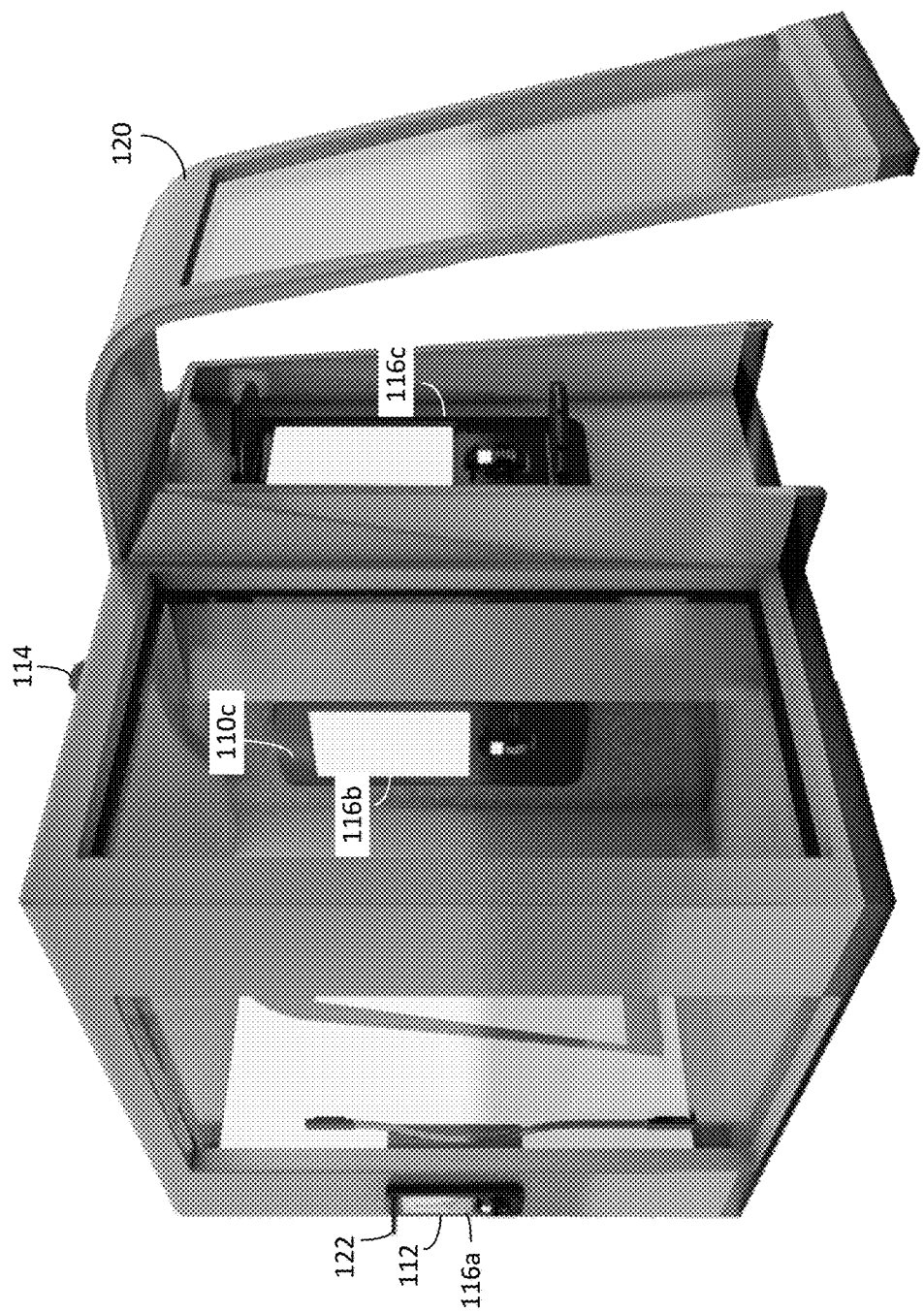

FIGS. 1A and 1B illustrate an example of a system 100 that can be a kiosk of other housing that can be uniquely associated with a use location in an exemplary embodiment. The housing can be a housing that can be affixed to the use location. The system can be implemented as a kiosk that can be mobile and include a housing having a controller. The housing 102 may be located at a use location and include a controller in communications with a computer readable medium. The housing can be physically associated with the use location, virtually associated with the use location or both. A location marker 104 can be affixed to the use location such as in a concrete slab or otherwise affixed at the use location. The housing can be removeable attached to the use location so that it is stationary during a first project or process but can be moved to a second project or process at a different physical location once the first project or process is completed. For example, the housing can be positioned at a trade show for collectibles or memorabilia transactions during that trade show and removed at the conclusion of the trade show. The kiosk can include an external area 106 that can be open to the environment. The kiosk can include a closed area 108 that can have a door allowing area 108 to be isolated from the environment.

For a location marker, in one embodiment, a transmitter such as a RFID can be associated with the use location by embedding it is a permanent fixture. The system can read the information from the location marker and associate its actual location with the use location. The location marker can include an alpha, numeric or graphical information such as a number, letters, barcodes, QR code, physical, plaque, sigh or geographic coordinates (e.g., GPS coordinates), passive transmitter, active transmitter, and the like. Each system can have a unique identifier and each use location can have a unique identifier.

FIG. 1A shows the system 100. The system 100 can include cameras 110a, 110b and 110c (FIG. 1B) for obtaining images of individuals, or other items at, entering, or leaving the kiosk as well as images of individuals along a perimeter. These cameras may capture biometric images upon which biometric recognition may be performed. Multiple cameras may be placed on or around the housing. The cameras may have biometric recognition and motion detection capabilities. System 100 may include one or more sensor assemblies 112 that can be biometric-based identification devices that may be used to confirm the identity of individuals entering, leaving or at the perimeter of the kiosk. The system 100 may include an antenna 114 for communicating with a network including a wireless network, Wi-Fi network, Bluetooth, quantum networks, cellular network (e.g., 4G or 5G network) and any combination. The system 100 may include a housing made of suitable weather resistant material, appropriately sealed to protect the internal hardware. The system 100 may include displays 116a, 116b and 116c that can include a touchscreen display, upon which information may be displayed and entered. The displays may include an integrated cameras that may be used to capture images and that may be used in performing facial recognition of individuals. The displays may include biometric readers, document scanners, currency dispenser assemblies, card reader, barcode scanners, document receipt assemblies and the like. The display may also include or operatively associate with one or more integrated speakers for providing audio output, a microphone for receiving audio information to facilitate two-way communications to a remote location. The scanners can be adapted for scanning items such as payment coupons, ownership records such as vehicle titles, identification material and other documents. The scanners may be, for example, a QR scanner, an Optical Character Recognition (OCR) or a bar code scanner in some instances. An overhang 120 may be provided to assist in decreasing glare and protecting some of the items on the housing from the weather. Speakers for providing audio output and a microphone to facilitate two-way communications with a remote location can be included in the system.

The external interface 116c and internal interface 116b can accept information such as loan information, tax information, and the like and may be displayed. In some embodiments, the information displayed may assume electronic form so that a video display is provided. In one embodiment, an access panel 122 can be included to allow or deny access to the interior area. Other location identifying information can be displayed such as location number, store number, lender number, certification number, use location and the like. In addition, the site address may be displayed on the system. The site address may refer to both the mailing address for the use location and other physically identifying information associated with the location.

The system 100 can be configured to be used by an individual at the use location. The housing can include an alarm indicator that can be actuated as described herein and can be internal or external. The access panel can include a biometric reader can include an iris scanner, fingerprint scanner, palm print scanner, facial scanner, or some combination. Any of the displays can be in proximity to input assemblies such as buttons. One or more cameras can provide a 360° field of view and include a wireless connection for transmitting images to a remote computer device. The images can also be used for input to the system including input allowing the system to identify delivered material. The system can include one or more second cameras such as webcams disposed at various locations around the system for capturing images. The lights can include motion activation and photoelectric activation. Speakers can be included to provide audio information to a user, inspector, or other party using or near the system. The audio information can include instructions, alarms, and the like. The system can include a secondary power source, such as a battery, so that when the main power is shut off, an alarm can sound, notification send to a remote computer device of other indication that the system or power source has been powered down. The access panel or other interfaces can include a hand scanner. The document scanner can be adapted for receiving physical documents, converting the physical document into a digital representation, and storing the digital representation on the computer readable medium or the persistent storage. The system can include a wired connection to remote computer devices of a transceiver to provide a wireless connection to remote computer devices.

Figure 1C:
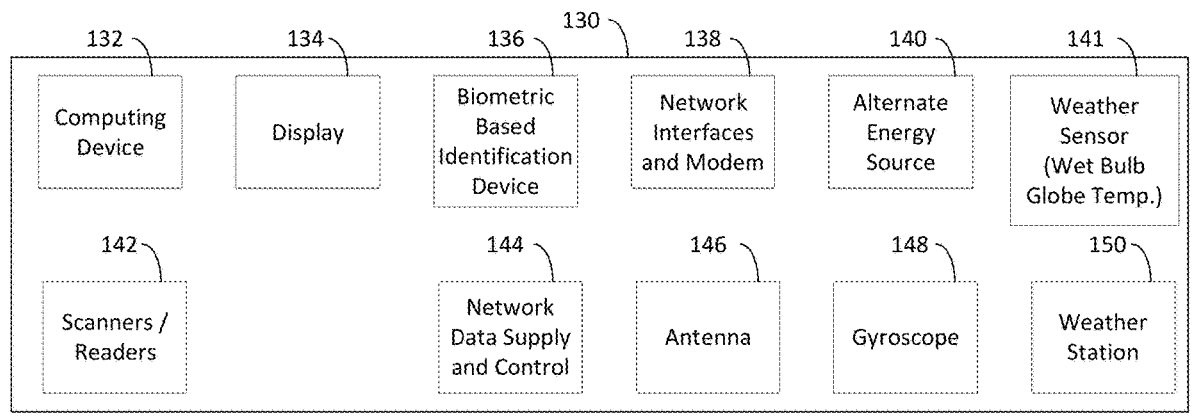
FIG. 1C is a block diagram of components of aspects of the system.

Referring to FIG. 1C, the system may include a computing device 132. The computing device 132 may take many different forms indicating a desktop computing device, a laptop computing device, a mobile computing device, an embedded system, a smartphone, special computer device, custom computer device, or the like. A display 134 may be integrated with the computing device 132 or as a separate device, such as a liquid crystal display (LCD) device, a light emitting diode (LED) display device or other types of display devices on which computer information may be displayed. One or more biometric-based identification devices 136 may be provided. As will be explained in more detail below, multiple biometric-based identification devices may be used. Network interfaces and a modem 138 may be provided. The network interfaces may interface the computing device 132 with a local area network or a wide area network wherein the networks may be wired or wireless. A modem may be provided to communicate telephonically or over cable lines with remote computing devices.

The system 130 may be implemented in a distributed fashion and may include an alternative energy source 140. For example, solar panels, wind turbine(s), a battery or the like may be used. In one embodiment, the alternative energy source may be physically affixed to the housing or in communications with the system or controller. For example, solar panels or a cable to a wind power source could be configured to provide power to the system and/or can be affixed to the system or housing. Alternatively, a power line leading to the alternative energy source may be connected to the housing and system to provide power to the system, housing, and associated components such as external power supplies.

The system 130 may include various scanners and readers 142, such as those described above relative to housing. The system 130 may include an internet data supply control 144 and a mechanism for turning the access to this service on and off under a programmatic control. Programmatic control may be provided to grant or deny access to such resources. The system 130 may include an antenna 146 for wireless communications signals to receive and transmit. The system 130 may include a gyroscope 148 to monitor any moving of the system. The gyroscope 148 may indicate motion indicative of whether someone is trying to move or tilt the housing or other component of the system. Logic may be provided to send a notification in such an event where the gyroscope indicates substantial enough movement. The system 130 may include a weather station 150 to measure current weather conditions, such as temperature, air movement, humidity, precipitation, barometric pressure, direct sunlight, and the like. Input from the weather station 150 may be used to inform decision making by the system in some instances. Alternatively, the weather may be collected via software, such as from a weather service or other weather source. Similarly, the system 130 may include a weather sensor 141. The sensor can be a wet bulb globe temperature adapted to measure, among other things, heat stress in direct sunlight, which accounts for temperature, humidity, air movement (direction and speed), sun angle and cloud cover (solar radiation).

Figure 2A:
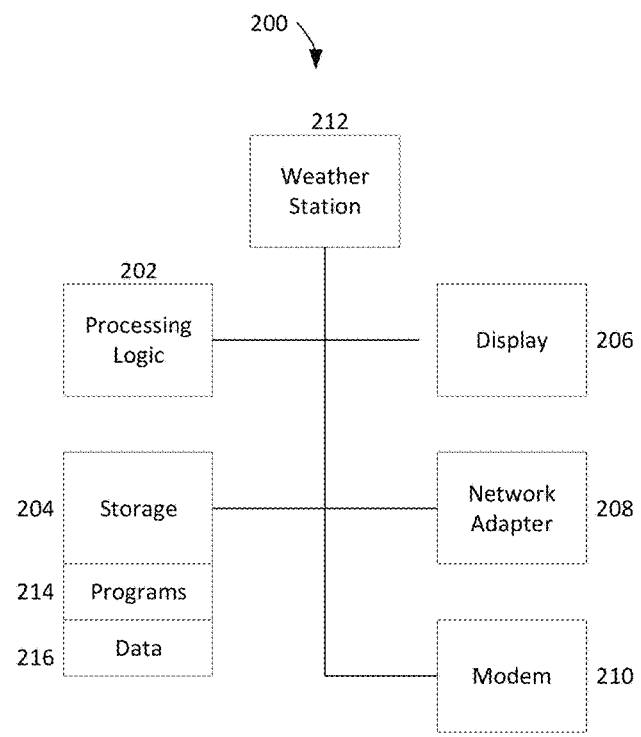
FIG. 2A is a block diagram of aspects of the system.

FIG. 2A shows an example of a computing device 200 for the system. The computing system may include processing logic 202, such as microprocessors, controllers, field programmable gate arrays (FPGA), application specific integrated circuits (ASICs) electronic circuitry, and other types of logic. The processing logic 202 performs the operations of the computing device 132. A storage device 204 may also be provided. The computer readable medium and/or data storage device 204 may take various forms, including magnetic storage, optical storage, etc. Storage capability 204 may include computer-readable media, including removable computer readable media, such as disks, thumb drives and the like, or disk drives, solid state memory, random access memory (RAM), read only memory (ROM) and other types of storage. The computing device may include a display 206, such as an LCD display, an LED display, or other types of display devices on which video information may be displayed. The computing device 200 may include a network adapter 208 for interfacing with networks and a modem 210 for communicating wirelessly, over telephone lines or cable lines with remote devices. The processing logic 202 may use information stored in the storage device 204. In particular, the processing logic 202 may execute programs 214 stored in the storage and may access and store data 216 relative to the storage device 204. The computational functionality of the system described herein may be realized by the processing logic 202 executing the programs 214.

Figure 2B:
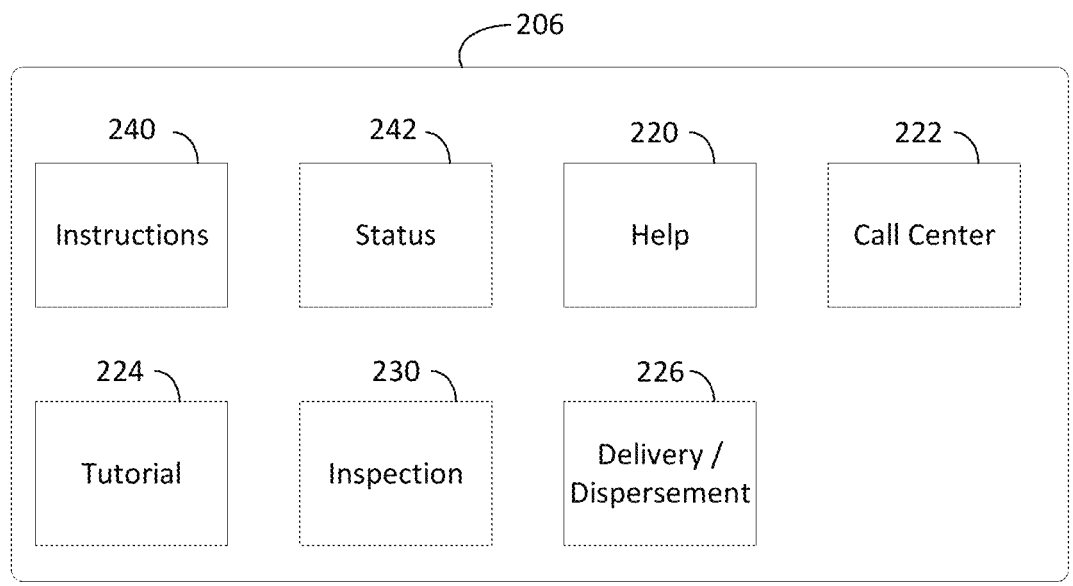
FIG. 2B shows aspects of a user interface.

FIG. 2B shows an example of a user interface on display 206, such as found in the housing 100. The user interface may include activatable elements. A user may depress these activatable elements or select these activatable elements using an input device, such as a mouse, keyboard, touchscreen, or the like, to activate the components. The display 206 may include a help element 220 that may be activated to obtain help information regarding use of the housing. It may also contain real time project or process plans. It may also include "how to" assistance including videos related to the various projects, stages, processes, and tasks performed at the use location. The user interface on the display 206 may also include a call center activatable element 222. Selection of the call center activatable element 222 may cause a call to be initiated with a call center so that the individual using the system 100 may have a telephone and or video conference with personnel at the call center. The call center can be connected to several third parties including a prior authentication individual or entity in the event that communications is needed. For example, a call can be made to verify or assist in the loan process. The user interface on display 206 may also include a tutorial activatable element 224. Selection of the tutorial activatable element 224 causes a tutorial to be displayed to teach the individual about operation of the housing.

Figure 2C:
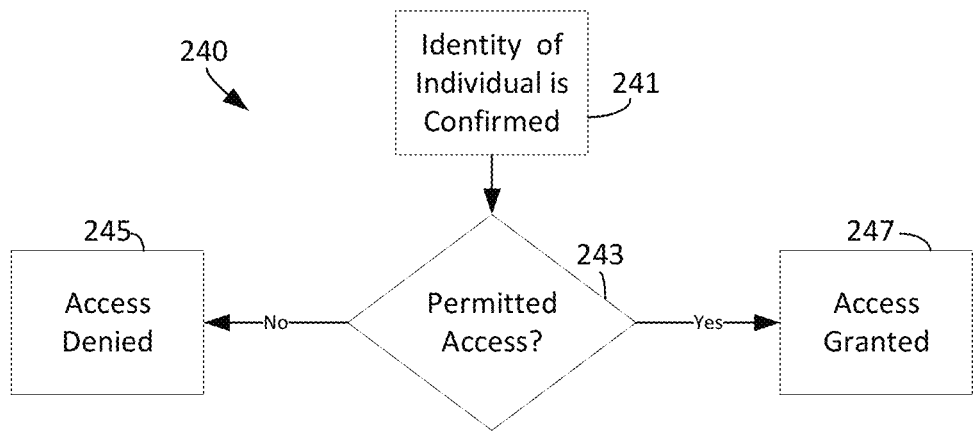
FIG. 2C shows flowcharts of aspects of the system.

Referring to FIG. 2C, the display may show instructions 240 for completing certain tasks or other information. A status of tasks and materials can be displayed at 242. For example, an individual can view the display and receive status information about materials such as anticipated delivery, route information, current location, or tasks as well as the status of tasks including performance steps, disbursement schedules, payment schedules, interest rates, loan status, and the like. The identity of an individual can be confirmed at 241, such as described above using biometric identity verification. The individual's information is accessed to determine if the individual is to be granted access to the system at 243. If the permissions indicate that access is to be granted, access is granted 247. In contrast if the permissions indicate that access is not to be granted, then access is denied 245. Permission information can be included in the individual information record. Permission information can be retrieved from the persistent storage or the system.

Figure 3A:
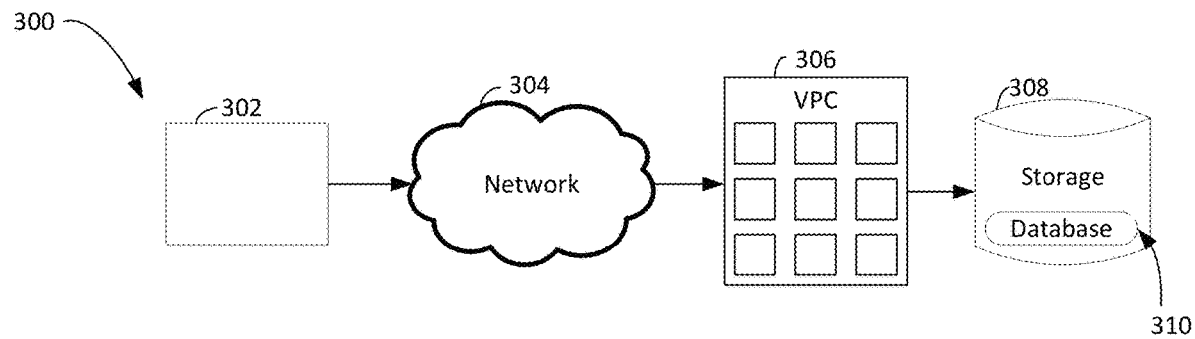
FIG. 3A shows an example of a communications environment.

As shown in FIG. 3A, the exemplary embodiments may be implemented in a decentralized computing environment 300 where multiple kiosks are connected and data may be shared and distributed across the systems and cloud computing. FIG. 3A shows one or more systems 302 that may be in communication with a remote cluster 306 via a network 304. The cluster 306 may store information received from the system 302 and provide added computational functionality. The network may be a wired network or a wireless network or a combination thereof. The network 304 may be a secure internet connection extending between the system 302 and the cluster 306, such as a virtual private cloud (VPC). The server may be a computing device and can be in communications with the site computer device. The cluster 306 may include access to storage 308. The storage 308 may include a database 310 in which information regarding a use location is stored in a consistent manner.

Figure 3B:
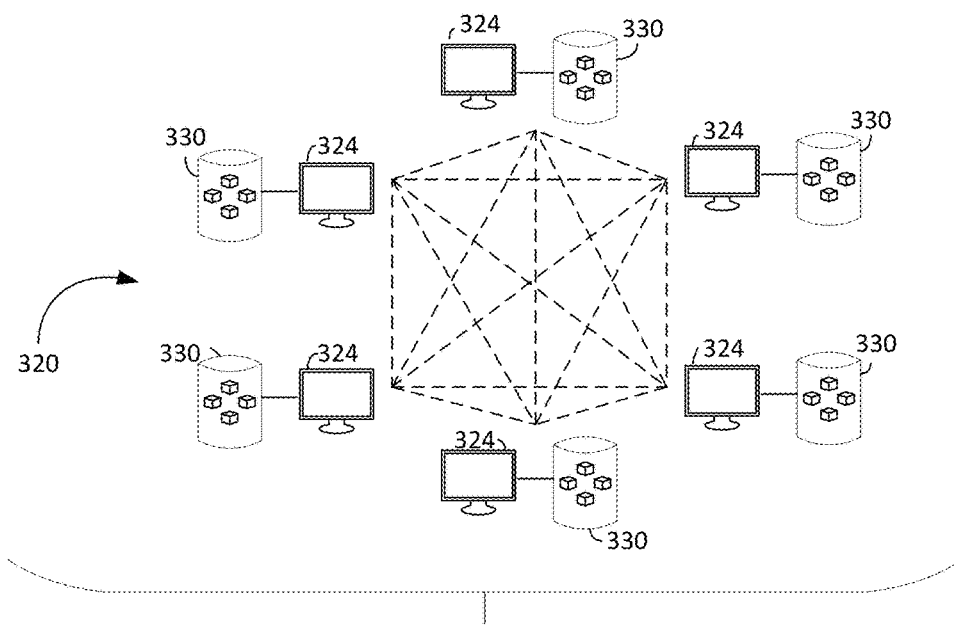
FIG. 3B shows an example of a persistent storage.
Figure 3C:
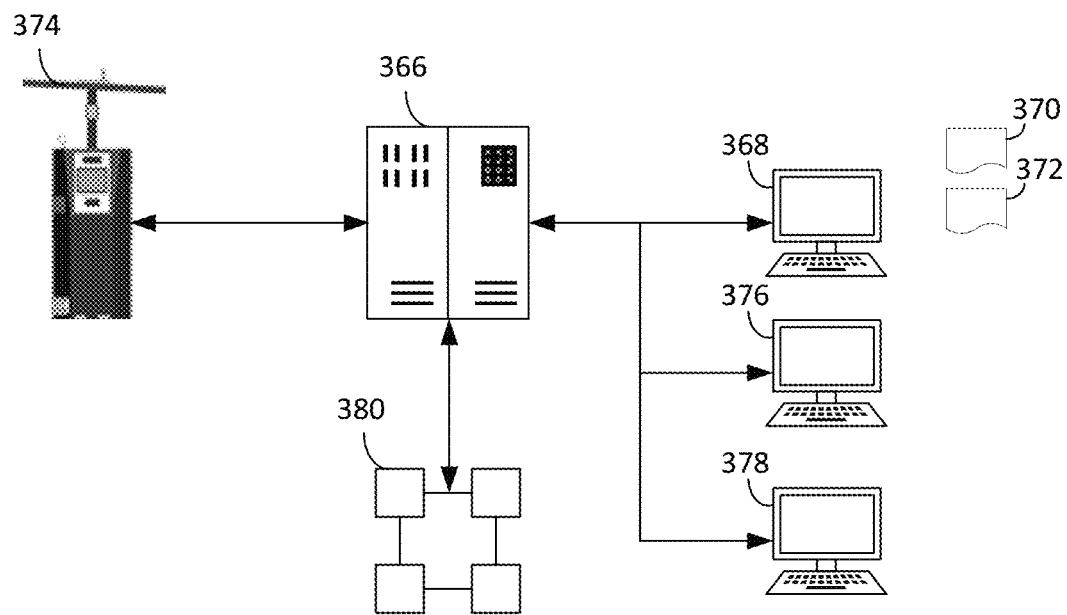
FIGS. 3C-3D show schematics of the aspects of the system.
Figure 3D:
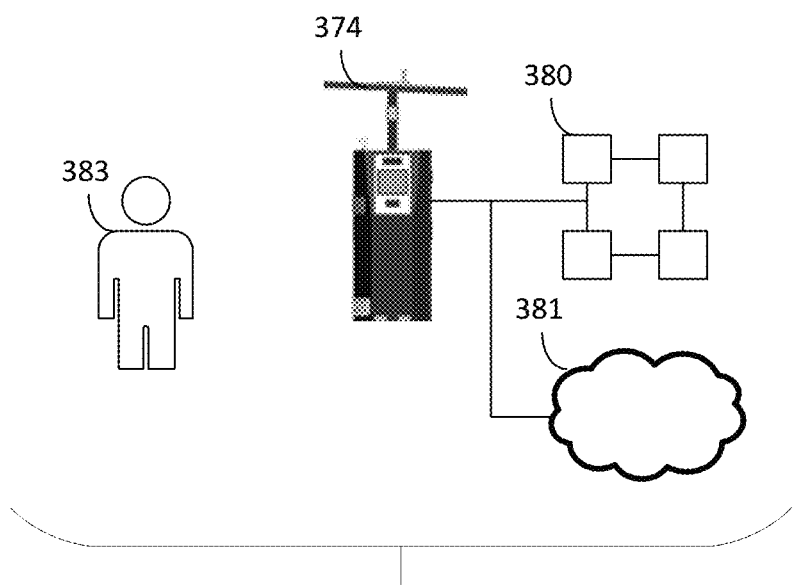

FIG. 3B shows diagram 320 of an example of a peer-based network where a persistent storage 330 is broadcast and shared among the nodes 324. This network may be resident in the VPC cluster 306 (FIG. 3A) or in the network 304 for example. The nodes 324 may represent computing resources, such as server computer systems or other computing systems with storage devices 330. FIG. 3C shows a kiosk 374 in communications with a server 366 that can be in communications with a distributed network or computer, storage devices of any combination. Third party computer system 368, 376 and 378 can be in communications with the server 366 and kiosk 374 so that information 370 and 372 can be shared with these systems. FIG. 3D shows a user 383 using kiosk 374 to access information from distributed storage 380 as well as transmit and receive data from a global communication network 381.

The information from a lender, borrower, financial entity, or other party can also be stored on the persistent storage and retrieved by the system. The controller can be configured for receiving an approval record from the lender representing the approval of a loan, creating a loan record representing the loan, creating a collateral record representing collateral inspected at or delivered to the use location, creating a disbursement record, creating a payment record, receiving verification information representing the loan amount was received by a borrower 383 (FIG. 3D) and storing information on the persistent storage.

Processes, projects, and task specifications, which may be needed for compliance with check cashing, loan requirements, regulatory requirement, insurance, specifications, inspection, and other requirements, can be received at 376 and requirements can be received from a requirements computer device 378 either directly or from the persistent storage. The requirements can include information by of from regulatory entities, lenders, financial institutions, and the like.

The various computer devices, including the server and site computer device (e.g., system, controller, and any combination), can be in communications with persistent storage 380. The persistent storage can include a distributed ledger, immutable database, block-chain structure, and the like. The communications between the various computer device, including the server and the site computer device and persistent storage can be a global communications network, wide area network, or local area network, delivered to a computer readable medium from one device to another (e.g., USB drive, CD, DVD) and can be wired or wireless.

Figure 4:
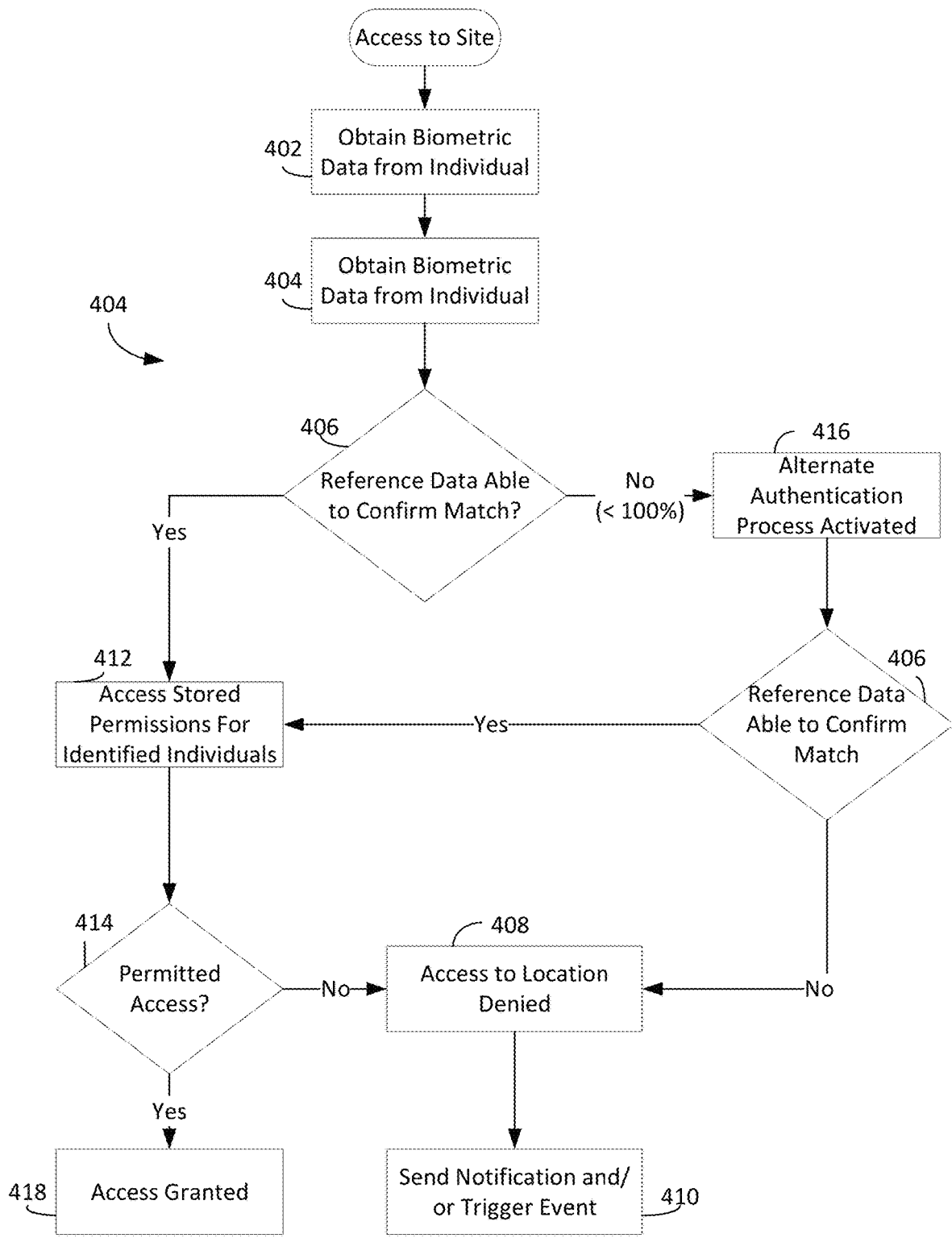
FIGS. 4-5 shows a flowchart illustrating aspects of the system.

FIG. 4 shows a flowchart 400 identifying steps that may be performed in exemplary embodiments regarding this functionality of the system. Initially, biometric data is obtained from an individual or other individual that is seeking access to the housing 402 for accessing the system. In some exemplary embodiments, a camera 102 may capture an image of an individual and facial recognition may be performed. The biometric data in one case is the facial image of the individual. In other exemplary embodiments, the biometric data may be, for example, fingerprint data, hand scan data, voice print data, retinal scan data or the like, gathered by appropriate biometric-based identification devices. The obtained biometric data is stored, and then previously stored data is accessed from storage to compare biometric data for known individuals and to attempt to identify the individual 404. A comparison may be made between the gathered biometric data and the known biometric data to determine if there is sufficient closeness for there to be a match. Information regarding the identity of the individuals for which the biometric data is stored is also stored in the storage device. A determination is then made whether there is a match or not 406.

If there is not a match 406, a manual process may be executed, or an alternative authentication process may be deployed 416. If this alternative authentication fails to produce a match 406, access to the use location may be denied 408. In addition, a notification may be sent to a responsible party and/or an event may be triggered, such as contacting security or law enforcement officials 410. If the alternative authentication process produces a match, the process proceeds to 412.

The system may store permissions for each person accessing the use location. These permissions may identify the dates and times where the individual is given access to the use location. In addition, the permissions may specify what materials and actions the individual can access or preform. These permissions may be accessed to determine the permissions for the identified individual 412. If the permissions indicate that access is permitted 414, the individual may be granted access to the use location and/or material at 418.

Figure 5:
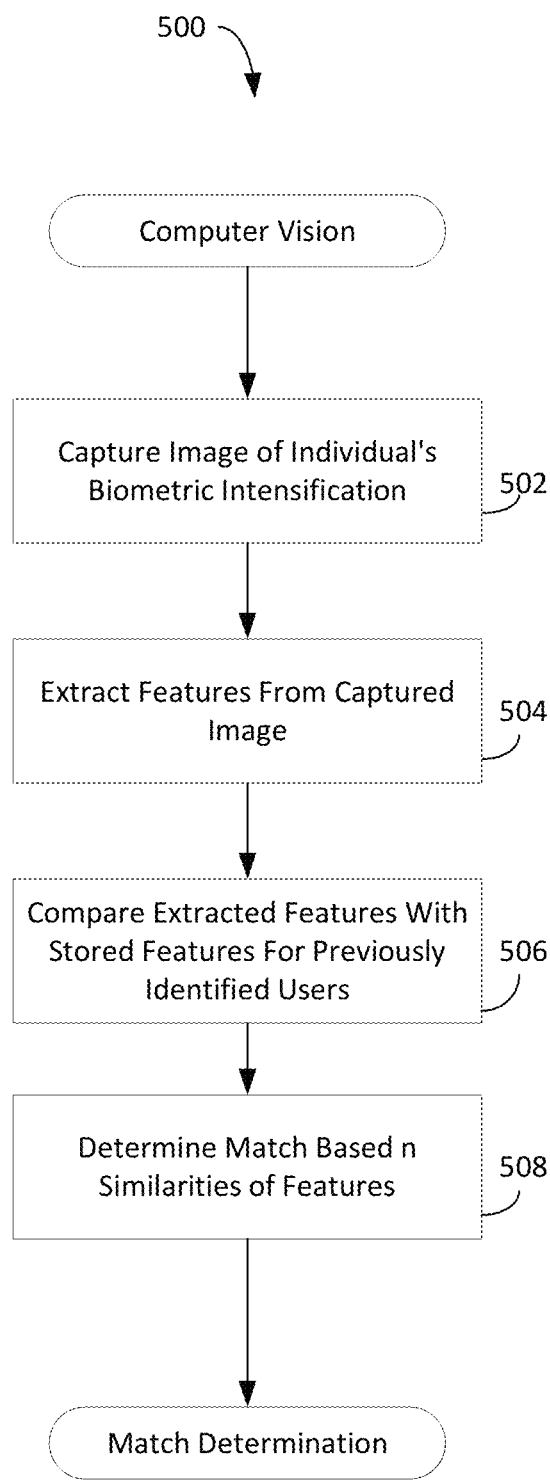

FIG. 5 shows steps that are performed in a case of computer vision for 402, 404 and 406 of FIG. 4. The flowchart 500 begins with 502 in which an image of an individual is captured for biometric recognition. This may be captured by several different types of image capture devices, including an intermittent video camera, still camera, iris scanner, facial scanner, fingerprint scanner, or other type of capture device. In the case where an image of the face of an individual is captured, identifying features may be extracted from the captured image 504. In other words, unique facial features that help to identify an individual are extracted from the image. The image may be filtered and/or normalized. The features are then compared with the stored features for identified individuals 506, determination is made whether there is enough similarity for there to be a match.

Figure 6:
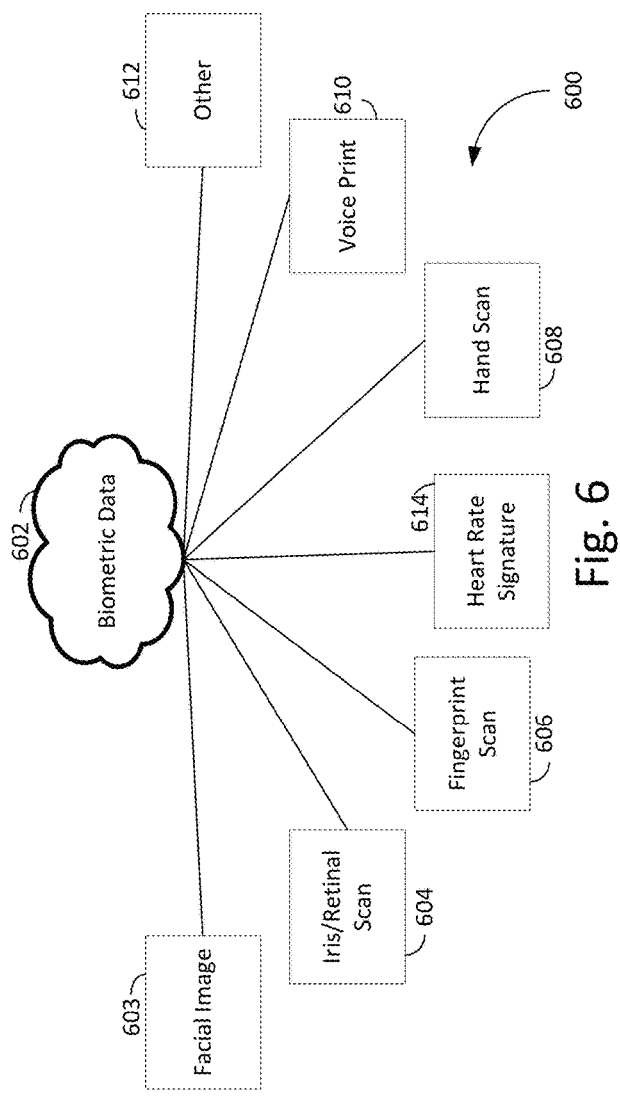
FIG. 6 shows various types of biometric data that may be gathered.

FIG. 6 shows a diagram 600 that illustrates various types of biometric data 602 that may be obtained by biometric-based identification devices at the use location to attempt to identify individuals. Biometric data may include facial recognition 603, an iris/retinal scan 604, a fingerprint scan 608, a hand scan 608, a voice print 610 or heart rate signature 614. It should be noted that other types 612 of biometric data may also be used in exemplary embodiments to help identify individuals uniquely. Also, an individual may be required to provide multiple types of biometric data in some instances.

Figure 7:
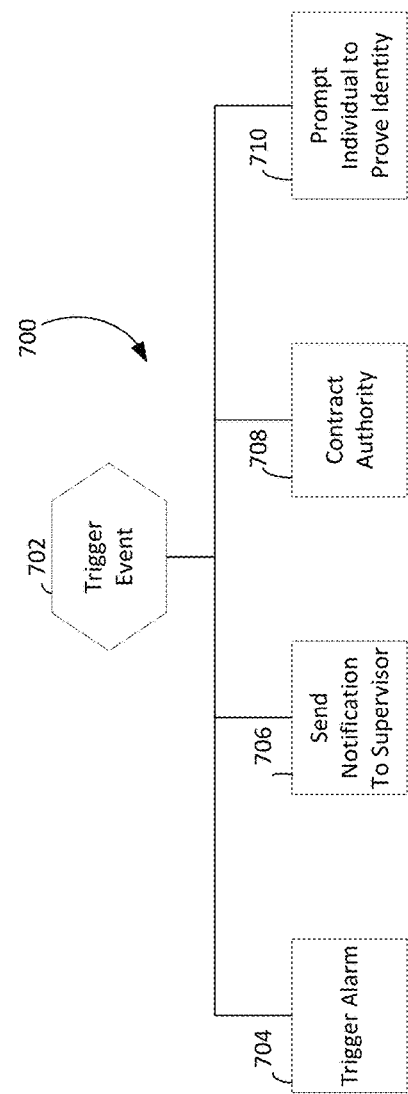
FIG. 7 shows the types of events that may be triggered.

When individuals attempt to access the kiosk location and are not granted access, certain events may be triggered (see 410 in FIG. 4). FIG. 7 shows a diagram 700 that provides an example of different types of triggered events 702. One type of triggered event is an alarm 704. This alarm may include visual alerts, audio alerts and any combination thereof. The alarm may be a silent alarm to individuals. Another event that may be triggered is to send notifications to a supervisor for the use location 706. The supervisor may, for example, receive an email, a text, a phone call, or another notification that someone is trying to access the site that is not permitted. A triggered event 702 may also include the contacting of law enforcement or a member of a security service indicating that an unauthorized party has tried to access the use location. Lastly, a triggered event 702 may include prompting the individual to produce proper identifying information to an official at the site or to a scanning device at the housing 100.

FIG. 8 shows a flowchart of the steps that may be performed to ensure that an individual gains access to the system and have been granted access to the use location. As shown in the flowchart 800 of FIG. 8, initially the individual has their identity confirmed, as has been discussed above 802. The system may offer an alternative touchscreen option to place a call to the appropriate party should the software fail to verify and otherwise authorized the individual. The individual may be prompted to interact with the display, such as the touchscreen 106B (FIG. 1) to register and to indicate whether they seek certain loans. In one embodiment, the user interface of FIG. 2B can be activated by the individual activatable element 228 so that access is granted to wearables, collateral, fiat currency and other items 806.

As shown in FIG. 9, a flowchart 900 shows some of the steps performed automatically and can be performed without notification to an individual. The process begins with the checking of the location 902 of an individual. A determination is made in 904 whether the individual is permitted to be at that location. If the individual is not permitted to be at that location, a response is triggered 906.

Figure 10A:
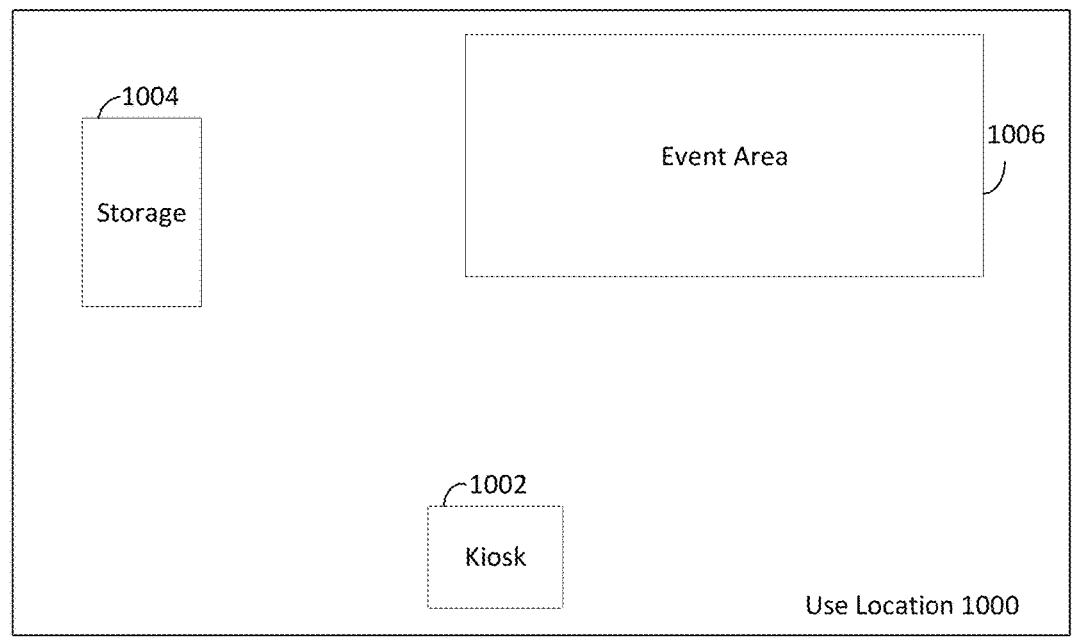
FIG. 10A shows a plan view of a use location.

To help illustrate an example of geofencing, FIG. 10A shows an illustrative use location 1000. The use location 1000 may include a kiosk or housing 1002 for the system as well as storage location 1004 that can be a building, trailer, shed or the like. The storage location 1004 may hold materials which can include collateral and other material. The use location 1000 may also include a task location 1006. The task location may be where tasks are performed such as pre-qualification verification, loan processing, loan approval, payments, loan satisfaction and the like.

Figure 10B:
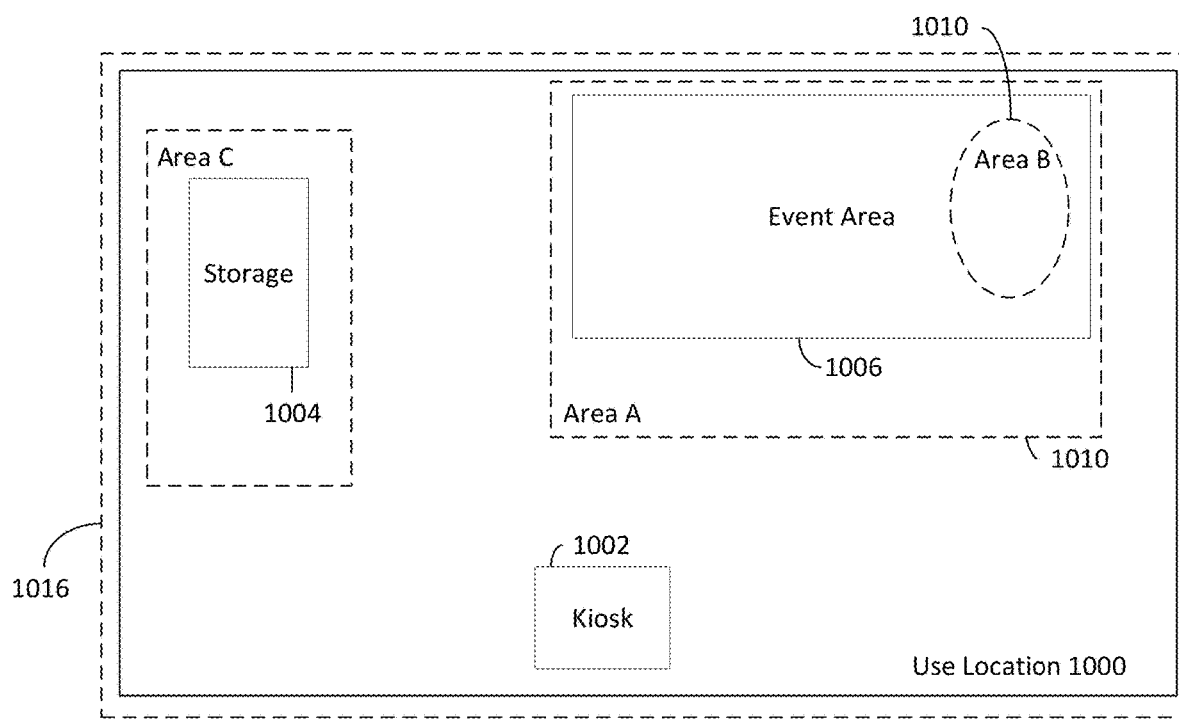
FIG. 10B shows a plan view with geofencing at a use location.

FIG. 10B shows an example of different areas that may be established for geofencing at the use location 1000. Area A shown a boundary 1010 may include the entirety of a certain use location 1206 (e.g., playing field). Area B 1012 may be a portion of the use location, such as where material is stored. Area C 1014 may be another location and area D 1016 may be the entire use location. Individuals may have access to none of these areas or to a subset of these areas, including all areas.

Figure 11:
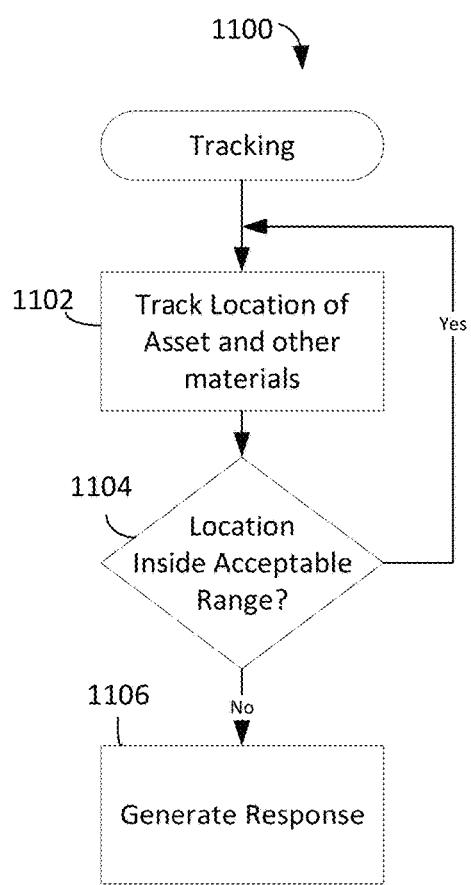

Referring to FIG. 11, the system may track collateral at the use location 1102. The system can check whether the location of the material. equipment, tools, or other collateral is acceptable or not 1104. For example, suppose that collateral is susceptible to damage if exposed to weather. If the collateral is outside, if may be unacceptable. Further, the system can determine of the collateral is removed from its proper location and if so, the system can generate a response. If the location is not acceptable as checked in 1104, a response is generated in 1106.

Figure 12:
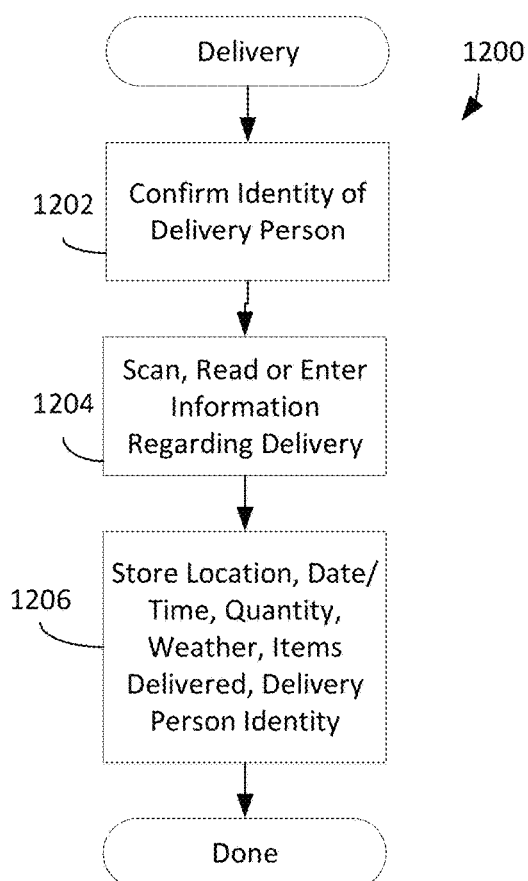

The system helps manage individuals, activities, and collateral that may be at a location. FIG. 12 depicts a flowchart 1200 showing steps that may be performed in relation to loans. The identity of lender or its agent can be is confirmed to indicate that the agent person is the appropriate party and is permitted to approve or otherwise manage a loan at the use location 1202. For example, an identification, biometric, serial number, or other identification indicator may be scanned or read. In addition, information may be entered by the agent person using the housing, such as by entering information via screen 106A (FIG. 1A) 1204. The location of loan processing, application, approval, disbursement, payment, collateral, status, and other event and the date, time and location may be recorded as part of the information that is kept regarding the loan. This information can be used to track and confirm loan approvals and status as well as to understand the conditions when the loan or related activity was performed.

When a transaction occurs, an individual (e.g., lender, borrower, agent, co-signer and the like) may interface with the system. FIG. 13 includes a flowchart 1300 illustrating steps that may be performed in such an interaction. Initially, the identity of the party may be confirmed using the biometric data 1302 or manually using the touchscreen on the system. The party can perform an inspection of the loan of associated events and material at the use location 1304. The inspector then accesses the system at 1306 and provide information about the loan we well as the system which can read information about the loan. The individual then may record notes and/or post certificates, notices, documents, or other information at the system 1308. Additionally, the party may use technology available via the system such as OCR scanner, camera, or the like to capture appropriate information the individual may include during the recording of the loan or transactions.

As has been mentioned above, a great deal of information may be collected and stored during the loan, process, or task for reference during authentication of transactions of a loan. FIG. 14 shows a flowchart of steps 1400 that may be performed in exemplary embodiments in relation to the information. The information obtained about the loan can be derived from many different sources may be stored on or referenced from persistent storage 1402. This information may help resolve disputes between parties concerning transactions, material, status, authentication, and the like. Since there is a complete record on the persistent storage of all transaction, individuals, activities, tasks, locations, and the like associated with the loan, these records may be accessed to resolve the dispute. Insurance providers may access these records referenced on the persistent storage to provide insurance or confirm claims. Inspection records may be accessed to confirm that proper inspections were carried out and passed. The information can be used to manage defaults and the appropriate response to a default.

A certification can be made a stored at 1404. The certificate of authenticity can be associated with a loan or part of a loan and its transactions and stored on the persistent storage.

The record may hold information such as the loan amount, date, time, lender, barrower, payments, interest, schedule, collateral, other individuals, locations, warranties, confirmation of conditions, insurance policy information, inspection history information, collateral ownership history, history of localized events; like weather and records of trespassing (such as images), bills of sale and receipts for collateral and loans and the like.

The information referenced in the persistent storage may also be accessed from a computing device of a party including collateral owner, seller, buyer, inspector, proposed buyer, insurance entity, creditor, customer, lender, borrower, and the like at 1406. In exemplary embodiments, information may be gathered from and sent to multiple parties including a managing company responsible for the management and oversight of a loan and its events.

Figure 15:
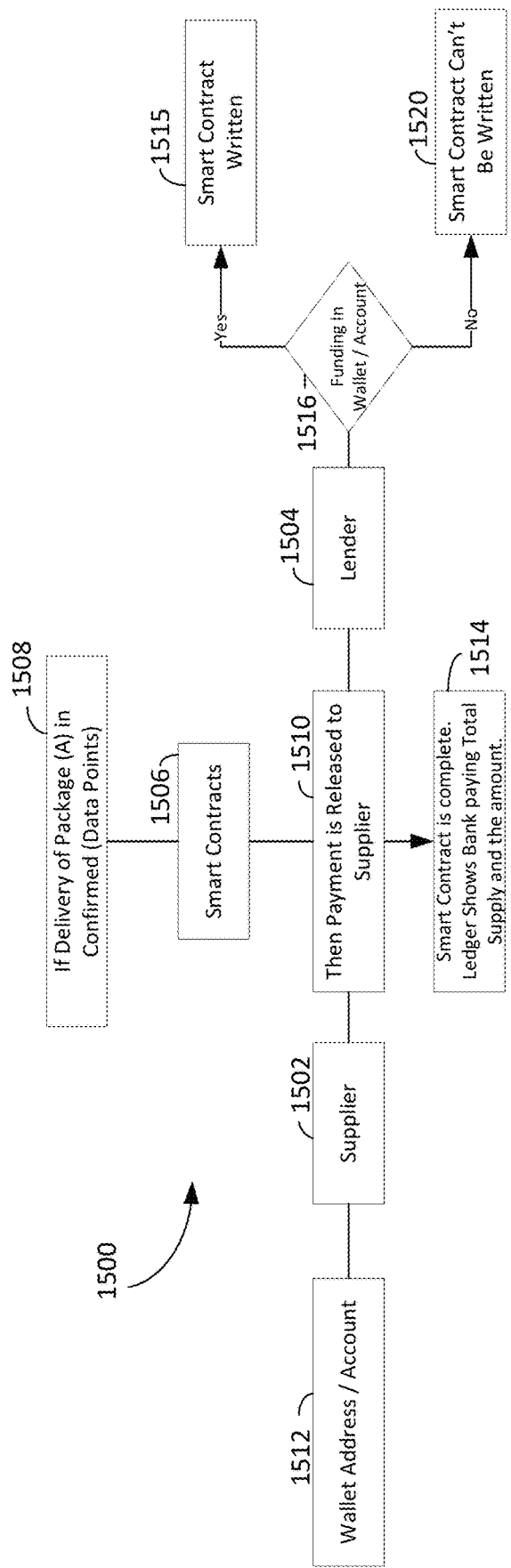

FIG. 15 shows a diagram 1500 of a first example of interactions relating to a smart contract for the loan. Suppose that the lender makes a loan at a use location. Further suppose that the loan is confirmed 1508 by information such as that gathered by the system as discussed above. The lender or other payor 1504 then releases payment 1510 to the borrower 1502. Payments can be made through third party funding, factoring, credit lines, loans, or other financial option to assist with financing and cash flow management.

The payment may be made electronically, such as through crypto currencies, like Bitcoin or Ether, or via a stable coin whose value is pinned to an item like a paper currency or the like. A cryptocurrency is a digital currency built with cryptographic protocols that make transactions secure and difficult to forge. Other Suitable forms of electronic payment includes Automated Clearing House (ACH) payment, Electronic Funds Transfer (EFT), card payments, other types of bank transfers or other types of electronic wallet transfer. In the case where crypto-currency is used, the crypto-currency may be delivered to the digital wallet of the supply company at a specified wallet address or account 1512. The ledger may be updated to show that the contract is complete 1514. Payment requires that the lender has sufficient funding in their digital wallet 1516. If not, the smart contract will not be written on the persistent storage 1515. If there is sufficient funding, payment is made, and the contract is written onto the persistence storage as complete at 1520.

Figure 16:
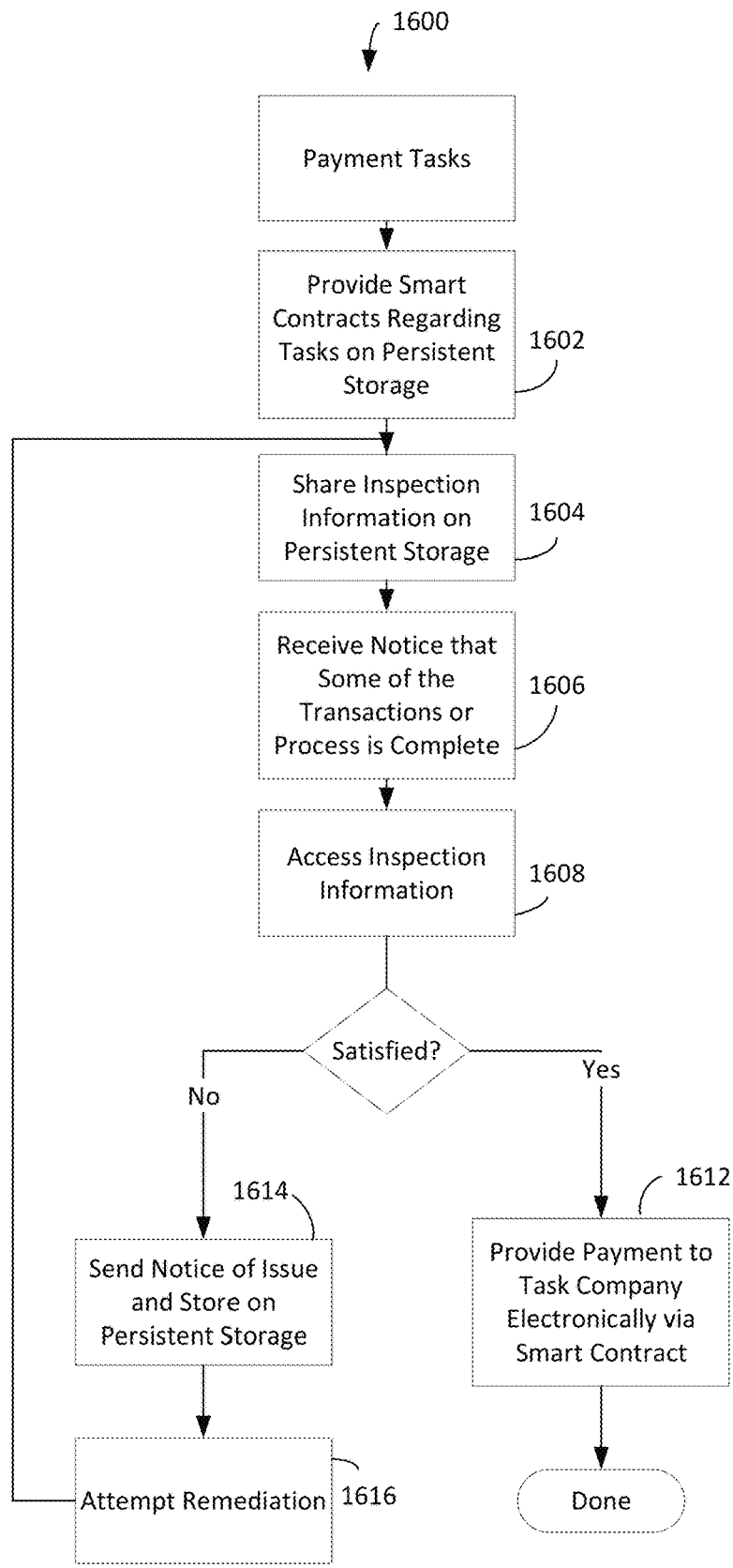

FIG. 16 shows a flowchart 1600 depicting steps performed for the loan project or process. Initially a smart contract may be initiated that uses the blockchain-based distributed ledger, where the smart contract is for at least a portion of the loan project or process 1602. An inspection of loan information and process takes place and information regarding the loan is passed through a hash function resulting in a hash value. The hash value may be referenced on the blockchain-based persistent storage 1604. The information may include, for example, the lender, borrower, financial entity, collateral, location, inspector, approval, date, time, an indication of whether the inspection and approval were passed, any notes from any party and an identification of any defects that cause a failed approval, loan, payment of satisfaction and how to remedy such defect. A notice is received at the system that a portion of the loan process is complete 1606. The inspection information is assessed 1608. If the inspection information indicates that the inspection was passed 1610, then funds may be provided 1612 to the borrower or received from the borrower via smart contract for the portion of the project or process. In contrast, if the inspection was unsuccessful, a notice of the failure and a notice of issues that need to be addressed may be sent, hashed, and resulting hash value may be referenced on the blockchain-based persistent storage 1614 for review by the lender and borrower. The borrower may then attempt to remediate the problems 1616 and repeat the above-described steps beginning with a new inspection and reference to a hash value for information regarding the new inspection on the persistent storage 1604.

To pair a loan and collateral with a virtual representation the system captures events at various points during the loan process. Pairing the physical material and activities with the virtual representation can include several elements or components. Included in the pairing process can be the physical observation of the parties, physical material, tasks, transaction, and then associate these items with a virtual representation. This verification provides trust that the virtual representation is accurately associated with the corresponding activity, take or physical material as a factor rather than simply trusting that the virtual representation is accurate. This system can use manual or automated processes to physically observe loan transactions and material and associate the transactions and material with the virtual representation from application to satisfaction or default remedy. Verification can also use the metadata that is associated with the interaction of transactions and physical items by individuals. The metadata that can be captured and placed into immutable storage can provide stakeholders an audit trail of history for the loan using a verified paired virtual representation. A similar process as described herein can be used for pairing a biometric identifier with an individual.

For example, when a loan is initiated, an application record can be created that captures the application event and can include metadata concerning the event and verification that the application is associated with an individual, location, and an application process. For example, a digital image of the application, individual and application process can be captured, and the images and its metadata of the image captured can be included in the virtual representation. The capture device and its metadata can also be captured and included in the application record. For example, a sensor having a GPS transponder, camera and transceiver can be used to capture the application event. The metadata of the application event can include date, time, location (e.g., GPS coordinates), individual image, lender, collateral, and any combination. Once received, the loan information can be processed. The loan processing can include retrieving information from the borrower's payment history, application frequency, approval rate, and like information. This infraction can be used for a determination of the loan terms that can include amount, length, payment schedule, interest rate, collateral requirements, default remedies and the like. For example, if the system receives employment or other income information from the borrower applicant, the system can determine risk factors. The risk factors can include paycheck to loan amount ration, location, date, time, history, and other factors. The system can then determine an initial interest rate and payment schedule. Upon the satisfaction of an initial loan, and in the event that the borrower application requests a second loan, the satisfaction of the first loan can be used to reduce the interest rate for the second loan. The system can have a structure for reducing interest rates upon detecting an established repayment history. Therefore, the borrower is rewarded for success initiation payment and satisfaction of loan using the system promoting recurring borrowers and increasing customer loyalty.

By verifiably pairing the loan with a virtual presentation, the risk of unintentional or impermissible rehypothecation can be reduced or eliminated. The collateral can be verified by multiparty chronological metadata streams that can be associated with a physical location. Because verifications using these streams are chronological, altering the information could require alteration of the metadata prior to and after the altered record. Therefore, the altered record would be inconsistent with the associated records potentially both temporally and geographically and an attempt to alter the record would be discovered. The use of a persistent storage further reduces the risk of alterations of records as well as increasing the verification of information. Further, pairing materials associated with the event, involving the material, interactions with the material and the associated metadata provide for a substantiated digital material, reduce, or eliminate risk and improve capital efficiency. Further, the pairing of materials facilitates commerce by allowing electronic transactions with assurances that the virtual representation used in the electronic transaction is paired with the physical material.

Verification, including verification of a loan event, can include verifying that the loan, its activity, collateral, and the virtual representation match and can be accomplished in a variation of methods including interaction with identification elements such as a tag, label, and the like, capturing an image of the material, capturing a video of the material, capturing a tag physically affixed or otherwise associated with the material, human visual inspection, and any combination. Identification of an individual performing or otherwise associated with an event can be captured by identification devices (e.g., cards, tags, RF ID) and biometrics including visual capture (e.g., facial recognition), voice recognition, iris scan, fingerprint, palm print and any combination.

A verification that the physical material and the retrieved virtual representation match can be performed using a capture device, individual verification, and a combination. The metadata associated with delivering the collateral can be captured and included in the collateral or loan record. The collateral or loan record can include information about the individual delivering the collateral and the collateral itself. The loan record can include information about the destination of the collateral. By capturing the events and verifying that the collateral is delivered to the lender or other agent of the lender and the virtual representation are paired, and stored on the persistent storage, the collateral, and loan information, and the virtual representation are paired from application to termination of the loan and a transaction record associated with the borrower is created.

Figure 17A:
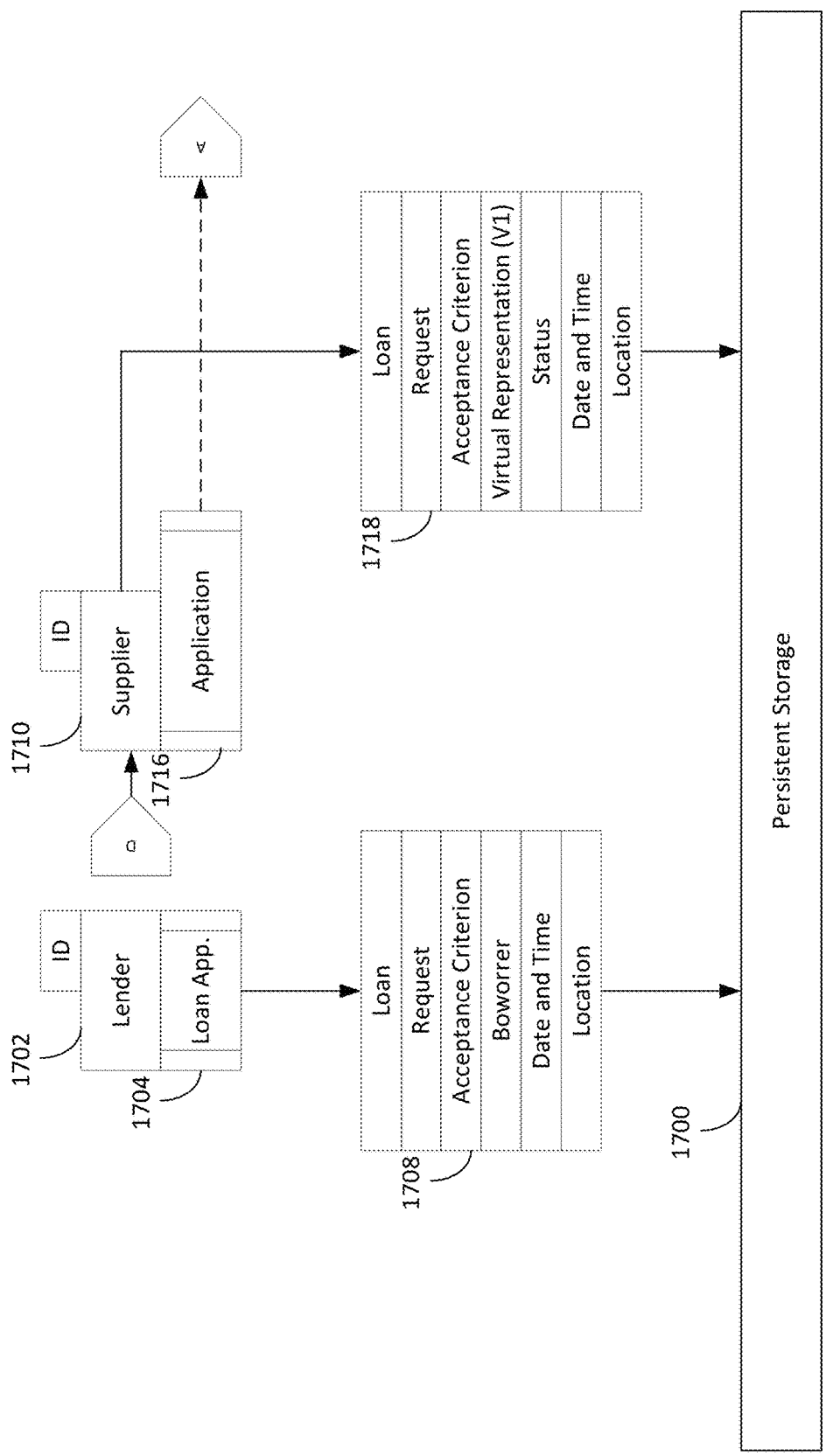
FIGS. 17A-17B shows schematics of aspects of the system.

Referring to FIG. 17A, an exemplary embodiment is shown. The persistent storage 1700 is accessible by a lender using a lender computer system 1702. The lender can have a unique ID associated with it. The lender can create loan application requirements such as amounts, borrower income, interest, schedules, remedies for default, other items, or activities. The lender can include loan approval requirements and other properties for the loan. The system can create a loan requirement record 1708 that can include information associated with the loan and application process that can be stored on the persistent storage that can be local or remote from the designer.

From the loan application record, an approval record can be created and stored on the persistent storage. The approval record can include a single component or multiple components. A lender, using a lender computer system 1710, can select or otherwise acquire loan application information 1716 identified from the loan application record 1712 that can be retrieved or otherwise received by the lender computer system from the persistent storage. The lender can verify that the application information from a borrower applicant matches the application requirement record, and the system can capture this event. Therefore, the information and the virtual representation ($V_1$) are paired by recording this event and associating the borrower. The information can be received by the lender, scanned, or otherwise identified with a sensor assembly, inspected by an individual and the lender process recorded. This can include capturing the metadata associated with the application including individual, amount, location, date, time, and process as stated herein. In one embodiment, the tag can include the following information:

| Description | Digits | Information |
|---|---|---|
| Locations | 19-20 | GPS XX.XXXXXX XXX.XXXXXX |
| User ID | 8 | SSN XXXX + Initials XX + Gender X |
| Date | 10 | XX/XX/XXXX |
| Time | 7 | Zulu XXXX:XX |
| Collateral | 12 | UPC/Barcode XXXXXXXXXXXX |

Figure 17B:
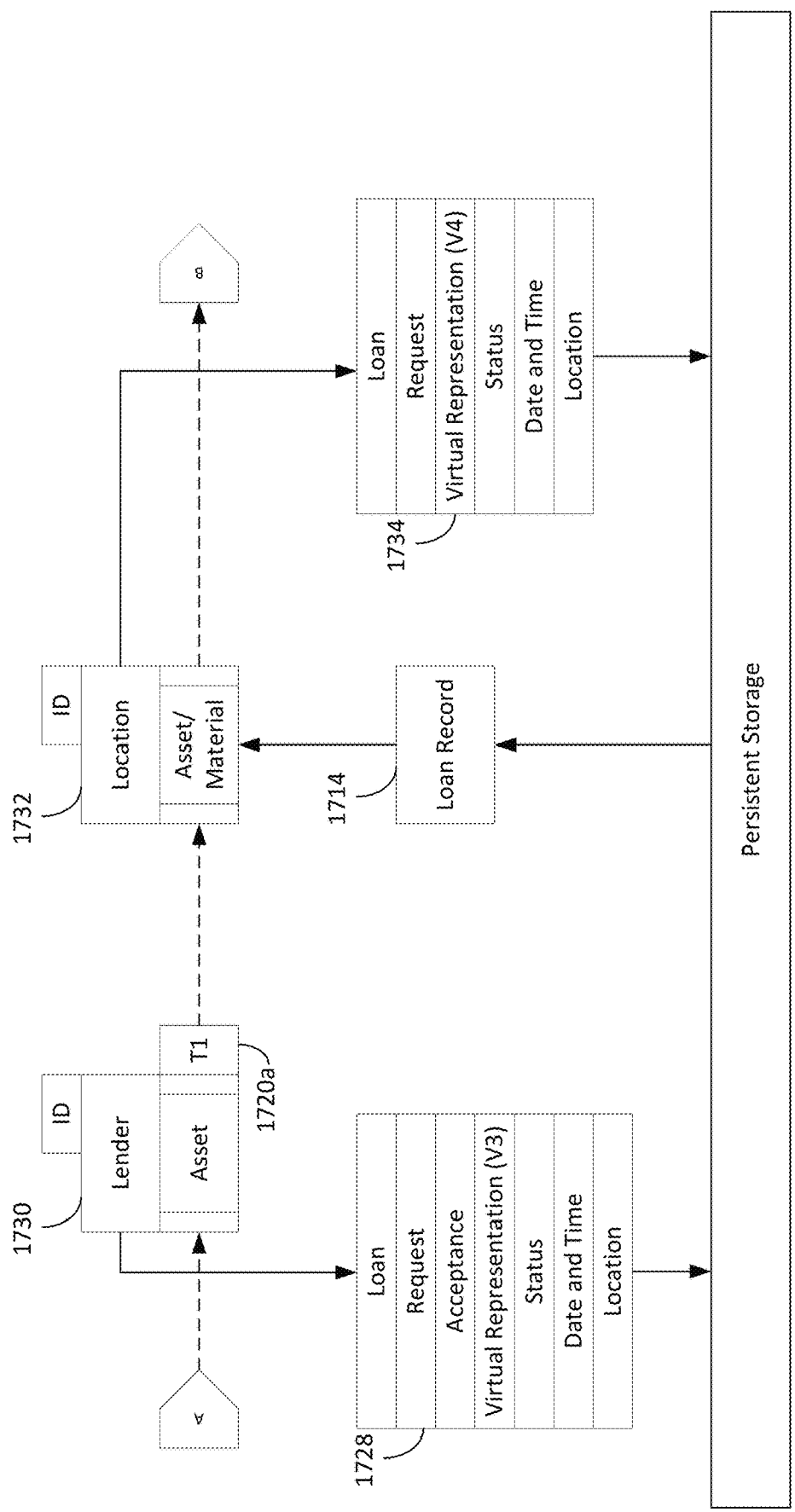
Figure 18A:
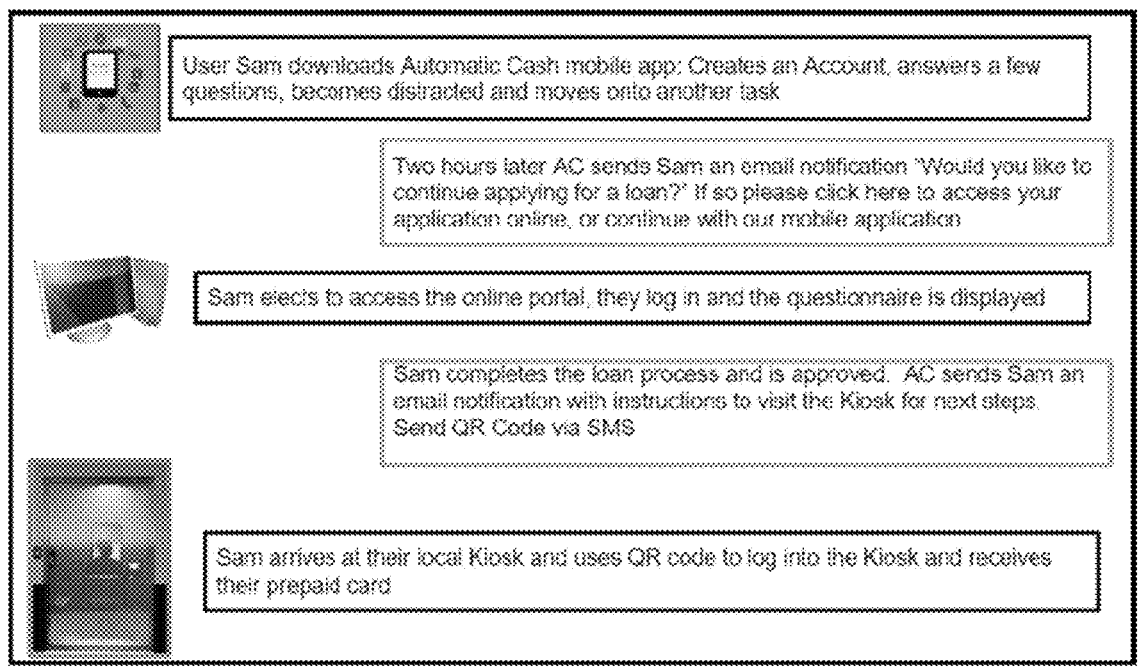
FIGS. 18A-18Q shows exemplary screens of components of the system.
Figure 18B:
Figure 18C:
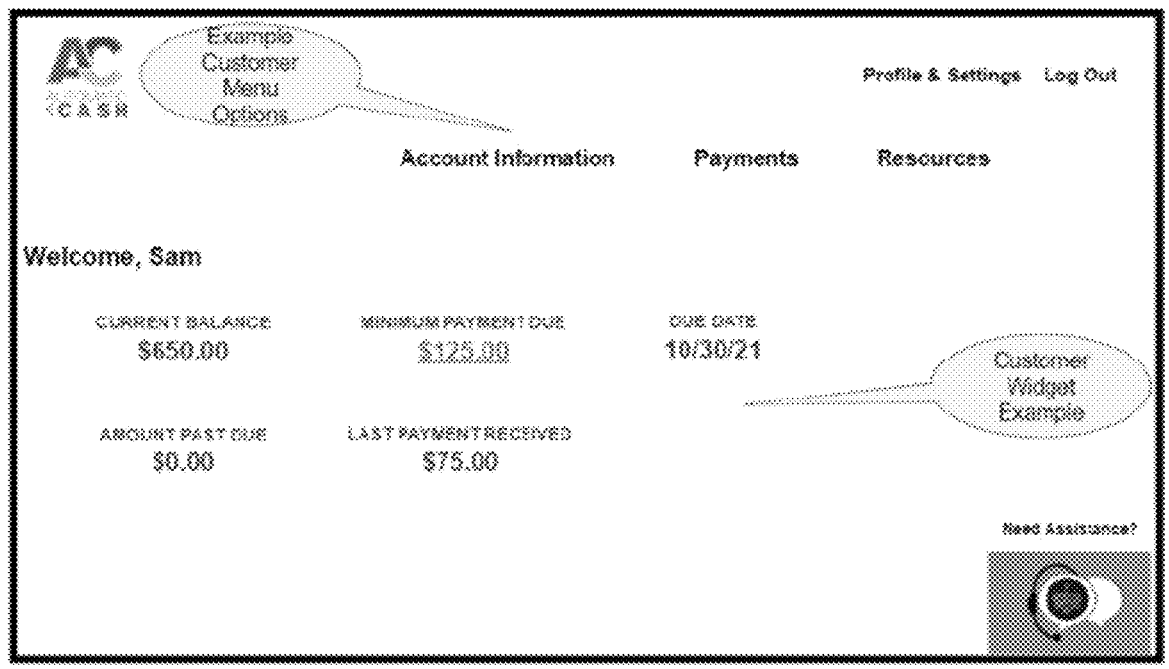
Figure 18D:
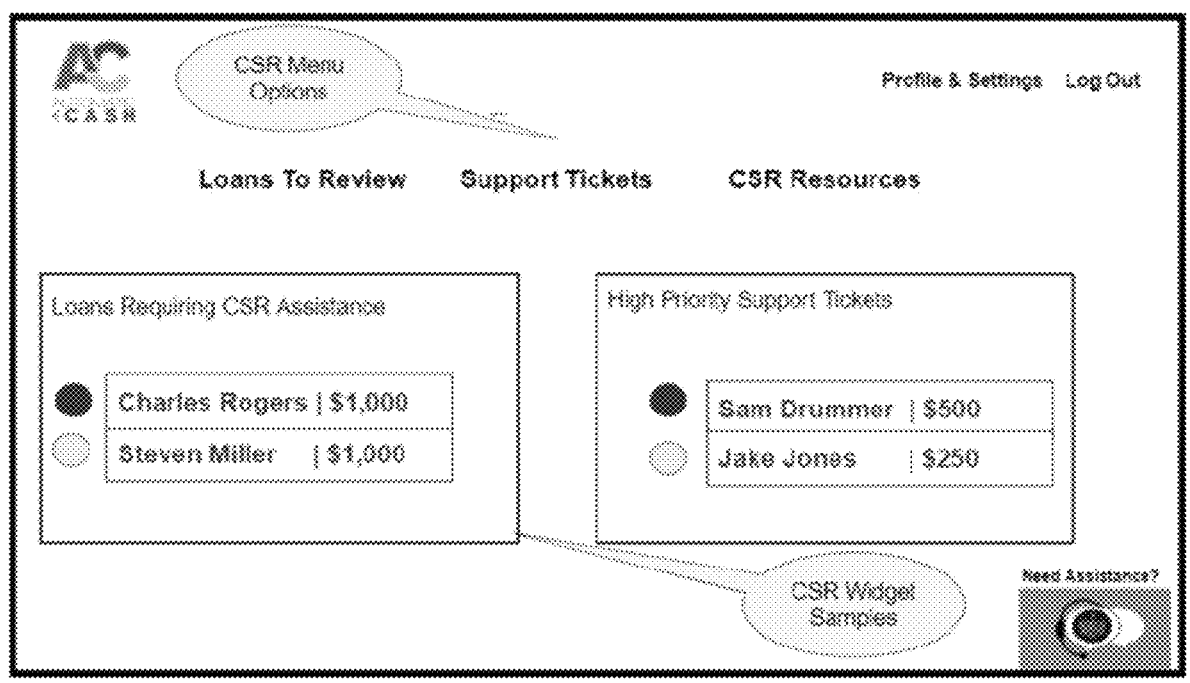
Figure 18E:
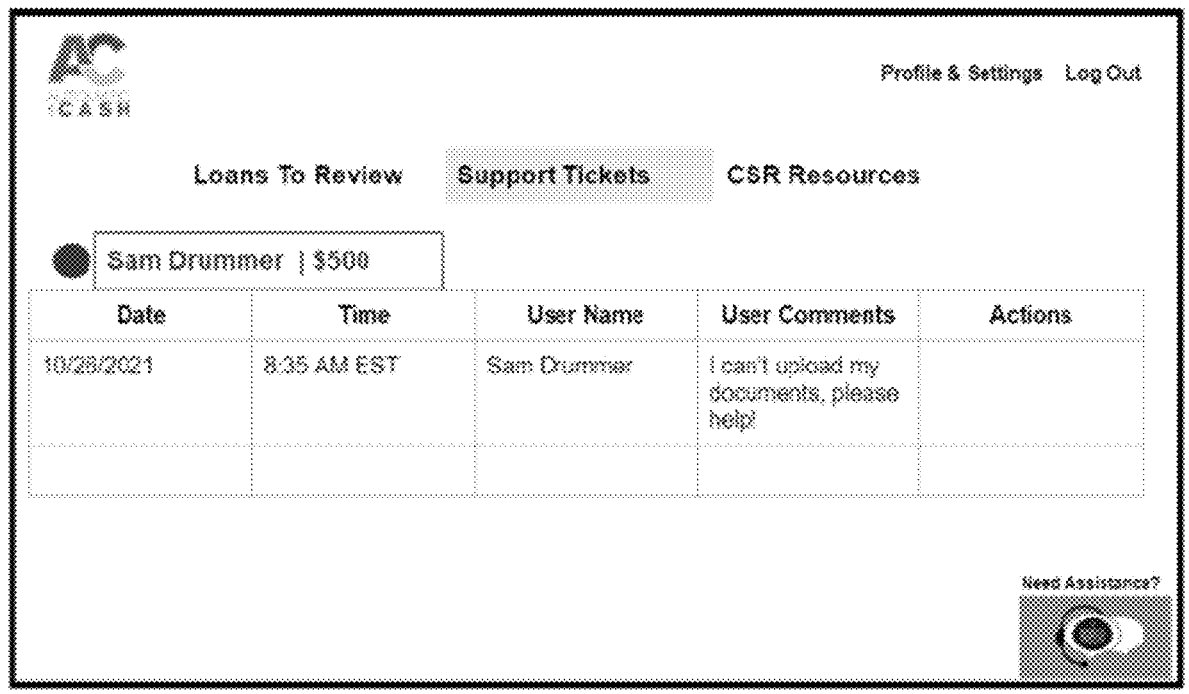
Figure 18F:
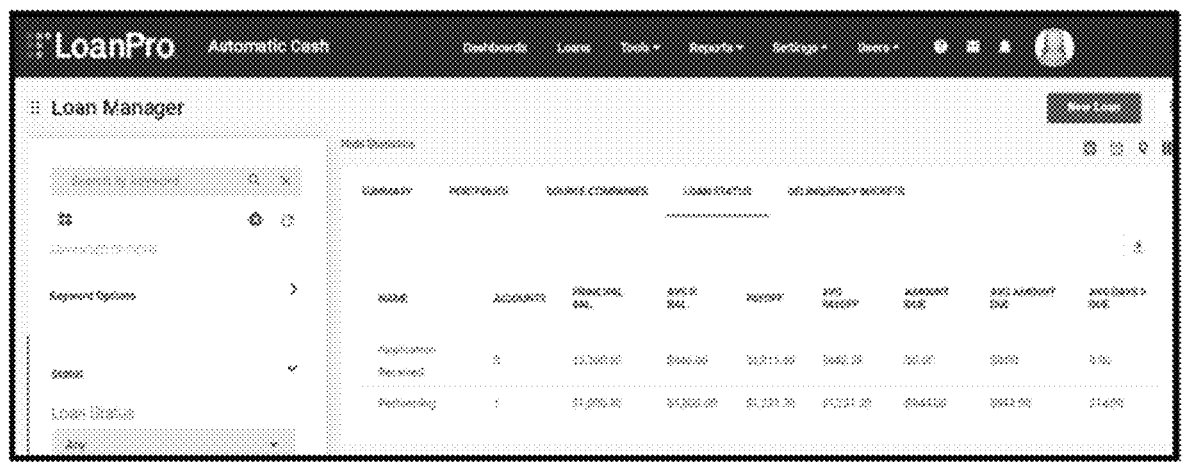
Figure 18G:
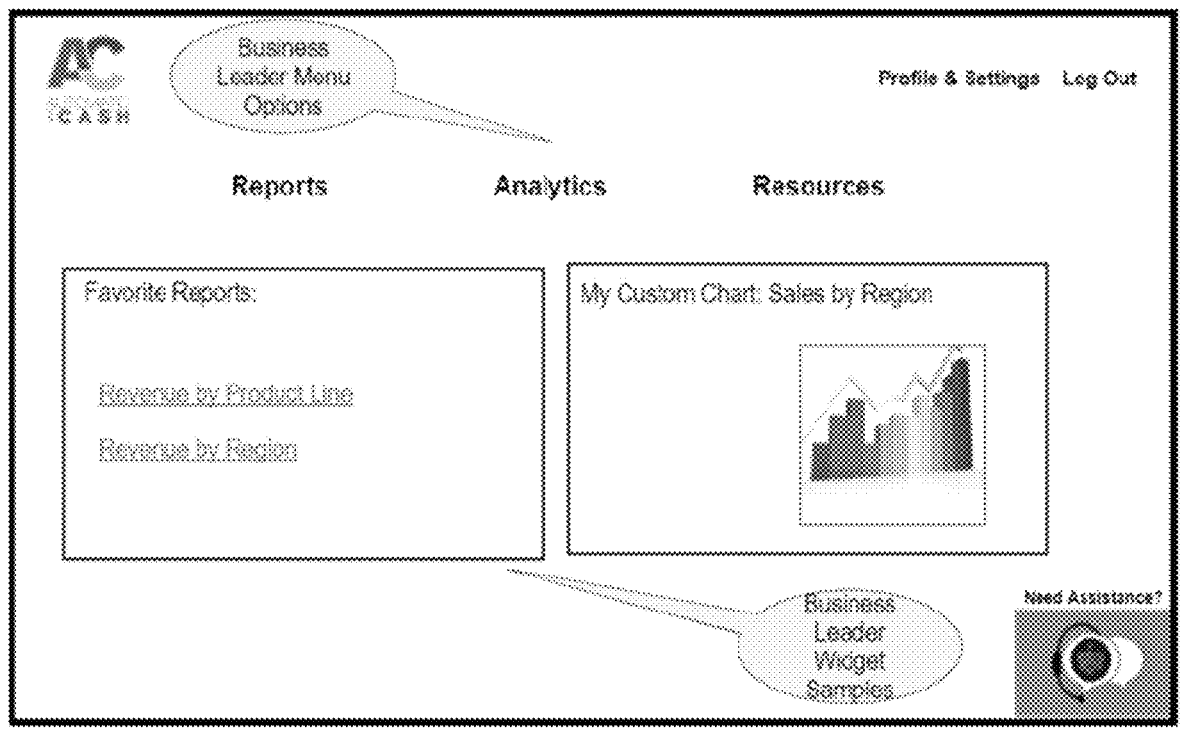
Figure 18H:
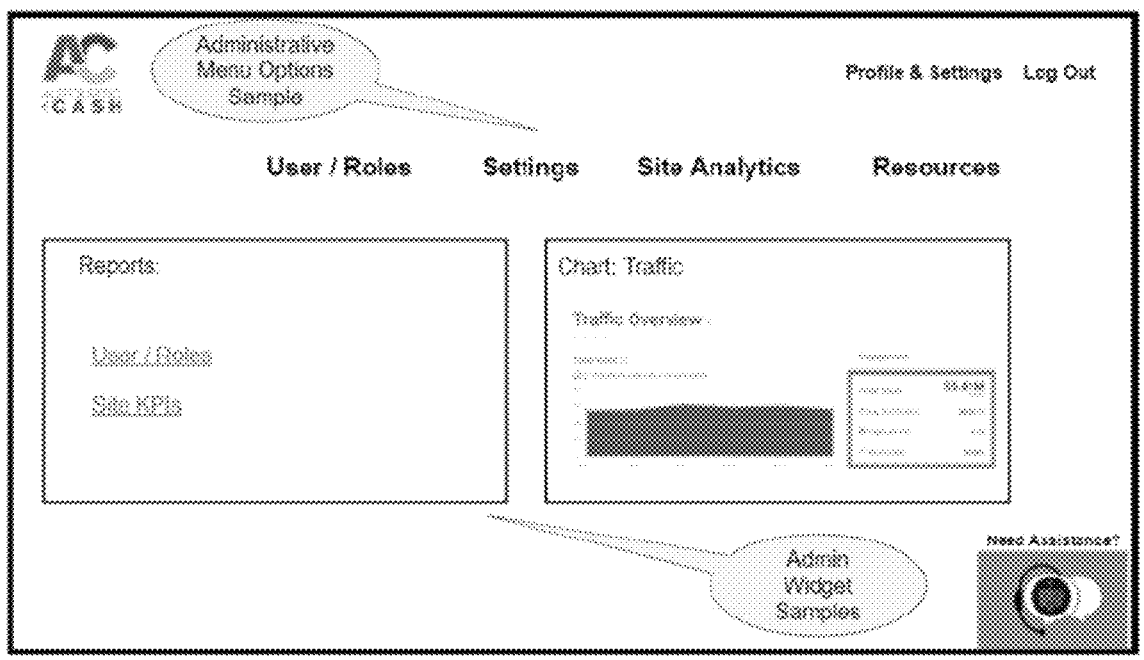
Figure 18I:
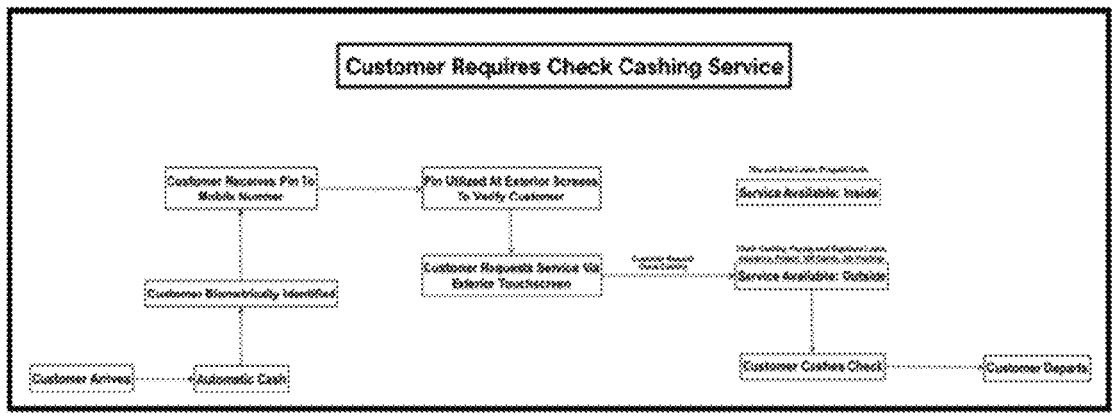
Figure 18J:
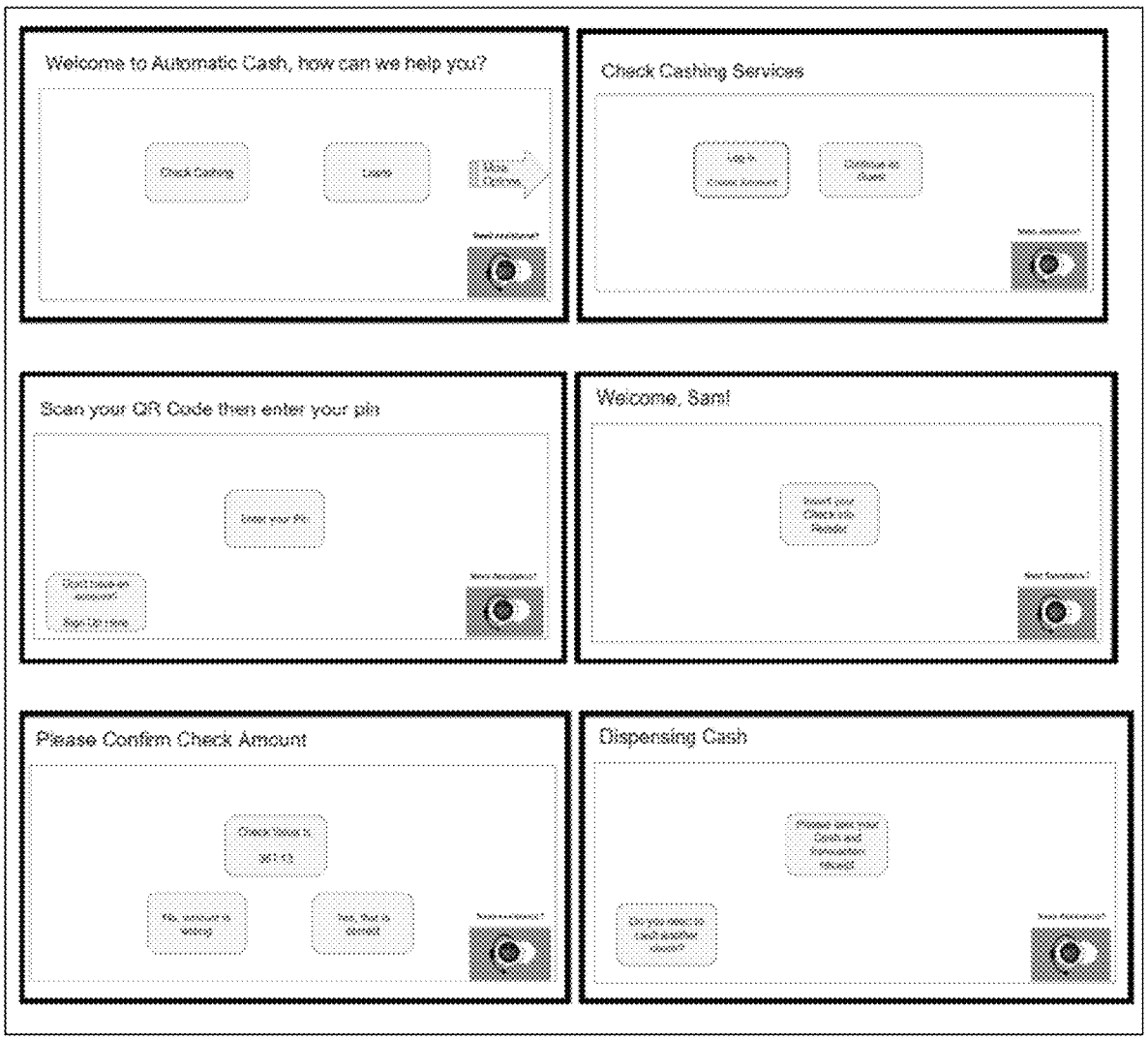
Figure 18M:
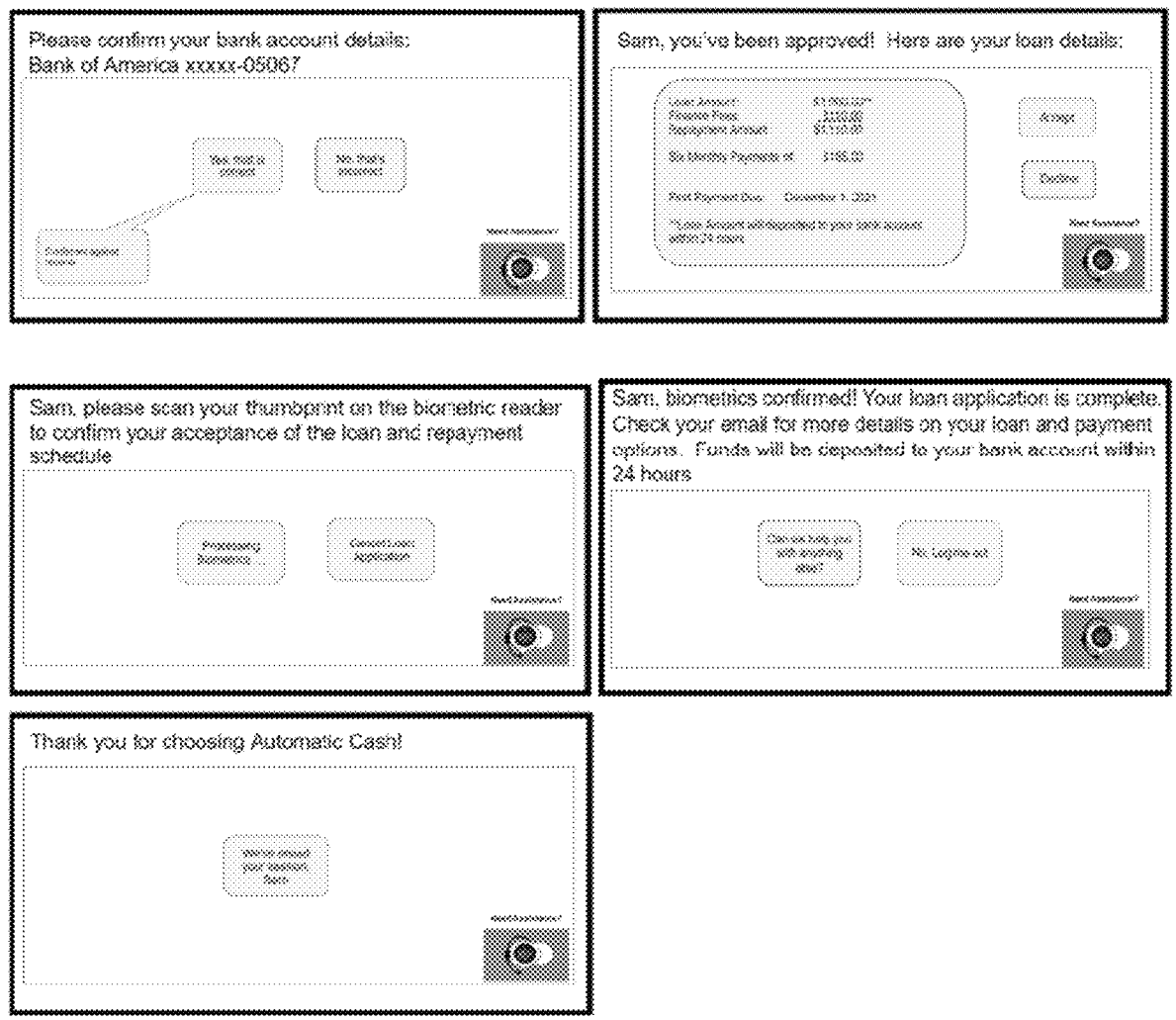
Figure 18N:
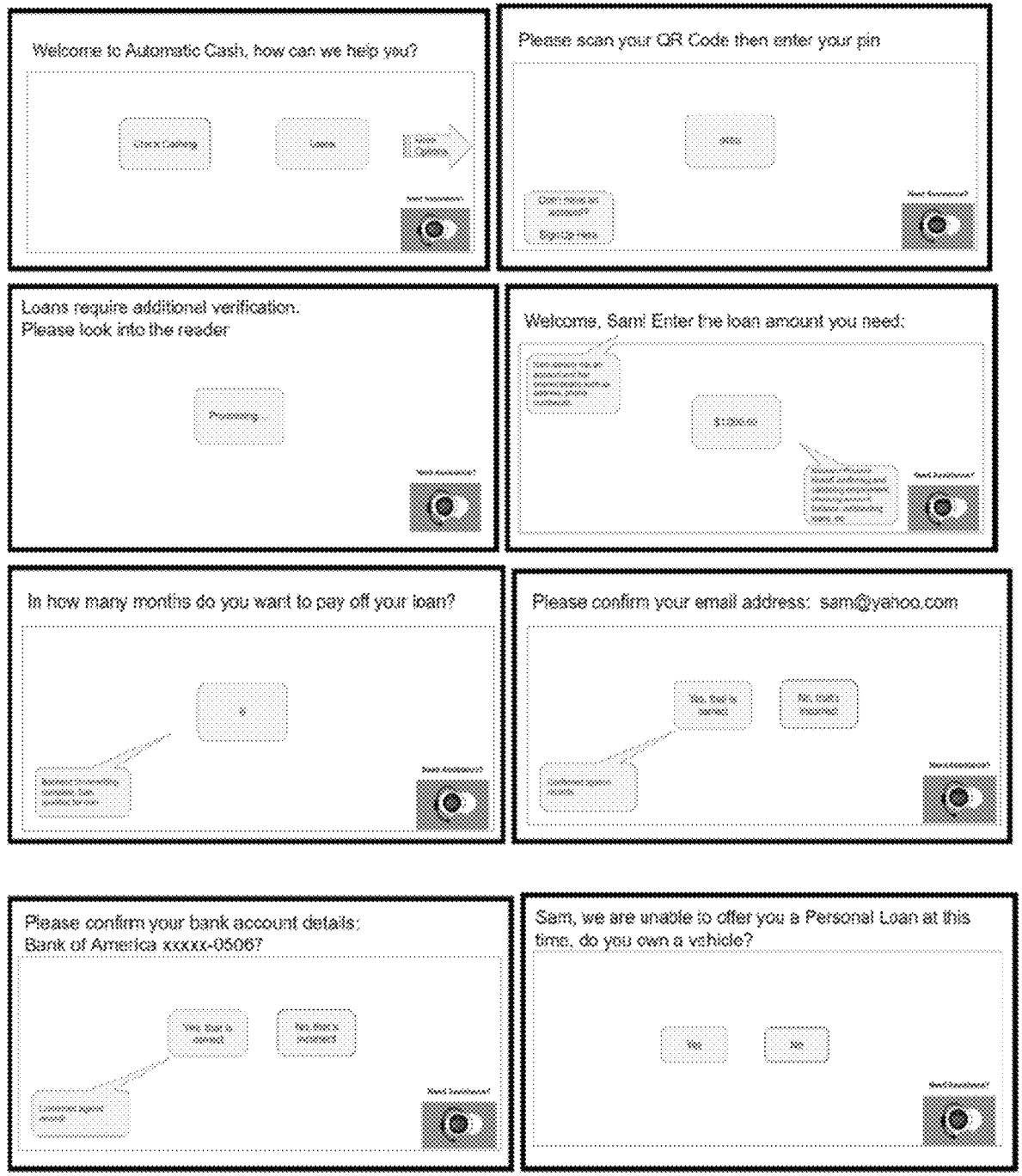
Figure 18O:
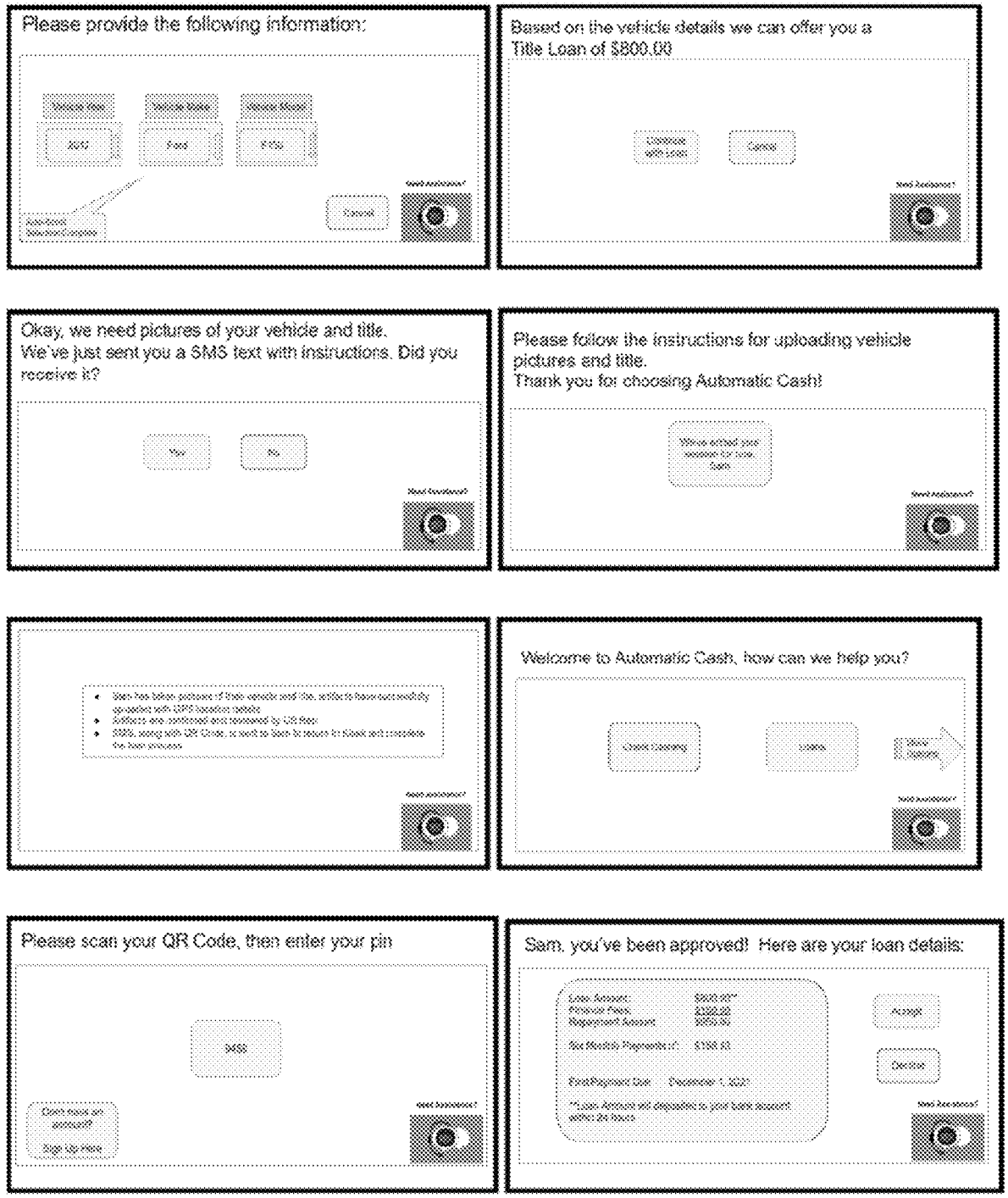

Referring to FIG. 17B, a borrower record 1718 can be created and stored on the persistent storage. The capture event can include a unique number and include the borrower ID, date and time, location, status, and any combination. The borrower record can include or reference an application, payment history, loan, income, employer, or specification record that can include the loan application and approval information.

Referring to FIG. 17B, a borrower can retrieve loan disbursements information from the persistent storage 1722 identifying the loan, pick time, location, and other information concerning the disbursement. The lender can verify that the disbursement matches the virtual representation of the application or approval record. If the collateral is used, it can be verified, the lender can physically capture the event, for example, by affixing its tag 1720a ($T_1$) to the collateral representing this verification. A borrower record 1714 can be created and stored on the persistent storage.

The lender can provide funds to the destination such as a use location or other location requested by the borrower. When the lender delivers the funds at the use location, the lender can capture this event by creating a disbursement record at 1728 a lender computer system 1730. The use location computer system 1732 can be used to verify that the loan properly implemented by retrieving the loan record 1714 from the persistent storage and using the loan record to match the loan transaction and parties. The system can create a use location received record 1734 that can include the loan information, virtual representation ($V_4$), status, date, time, location, other metadata, and any combination. The lender, borrower, individual at the use location, or other party can physically inspect the loan information and collateral and verify that it is matches the virtual representation stored on the persistent storage. This verification can be included in the information that is stored on the persistent storage by the shipper and an individual or system at the use location.

The system can receive payments, authenticate payments, or other activity. The system can verify the information using the sensor assembly including capturing information about the material, individual, event and the like. The unique identifier can be a number, bar code, alpha numeric characters, QR code, RFID, beacon, lot, size, sticker, tag, hologram, label, wireless transmitter, wireless transceiver, physical feature, and any combination.

The system can be used to retrieve the loan or other records from the persistent storage. The loan record can be used to match the collateral delivered to the use location to verify that the collateral is properly associated with corresponding loan. The use location can add tag to the collateral, or use other verification methods described herein, to capture the event and the material. The system can also capture the material and corresponding event or significance at by associating a tag to the material. A collateral record can be created, modified, stored or any combination on the persistent storage. The record can include the event, location, description, virtual representation, date, time, location, other metadata, and any combination. The system can generate and submit for filing a lien of other encumbrance for the collateral to the appropriate regulatory authority.

Once completed, the loan can be satisfied. The loan record can include final payment, return of the collateral, or other disposition of the loan and a satisfaction record can be created and stored on the persistent record. If the collateral needs to be delivered, a shipper can use a shipper computer system to retrieve the shipping record, collateral record, loan record, or other shipping information that is used to identify the origin, locations, collateral, pick up time, delivery time and other information associated with the transportation of the collateral from one location to another and from one owner to another.

The system described herein can pair the physical material (e.g., collateral) with a virtual representation. Failure to pair the material with the virtual representation can negatively impact areas such as authentication, certification, fraud prevention, and the like. Tracking, management, and verification of material and materials to ensure authenticity and use and manufacturing is an important aspect to many materials and their valuation. Tracking and record keeping during the life of a material from its creation to use can be difficult to perform without the ability to pair the material with ah virtual representation.

Systems at multiple locations may be interconnected using image capture devices, RFID, QR codes, barcodes, biometric scanners, still cameras, video cameras, and the like to identify individuals or machines that are performing verifications during the process. Further, multiple individuals or machines are performing verifications so that there is not a reliance upon any one entity for verifications. The processing of capturing data, including images, from the multiple systems at multiple locations can be used to improve the verification of proper material and materials as well as to pair the physical items with the virtual representation.

This system uses hardware and software to provide for streamlined, automated and secure financial services to user including the underbanked and unbanked population. Kiosks (e.g., physical, autonomous locations) can be used to provide the system as these can reduce the cost of lenders maintaining real estate and personnel and are in contrast with traditional physical branches and offices. A web portal can provide a backend engine that can assist with maintaining user account data (including biometrics and GPS anchoring of loan data), underwriting logic, loan management and other financial services. Mobile devices provide users an alternative option to the web portal to access specific elements of the financial services offerings and manage their account. The system can be adapted for managing user enrollment, data collection, underwriting and administration of loans, notifications, reporting and analytics. An associated web portal can be an information source for the system (e.g., kiosk and web portal application).

The computer readable instructions as a kiosk, onsite server or offsite server can be adapted for providing a web portal consumers allowing for transactions (e.g., check cashing, title loans, consumer loans, payday loans, utility payments, and job offers, facilitate kiosk integration with a web portal for bi-directional transfer of data based on defined product/services, facilitate mobile integration with a web portal for bi-directional transfer of data based on defined product/services, retrieve and use external data for determining approval of financial services (e.g., loan approval, terms and amounts), configure underwriting workflows including the ability to define and calculate underwriting algorithms for loan process; including the ability to define notification points for email/SMS and QR codes, allow ability for external users to configure an account and make loan requests, maintaining in data store biometrics and/or GPS logistics of the account creation event, allow external users to upload pictures and identification via web portal, validating and maintaining in the data source of biometrics and/or GPS logistics of artifact event, allow external users to make payments against their account utilizing payment methods available, maintaining in the data source mobile biometrics and/or GPS logistics of payment event, integrate with third party applications to retrieve, collect and store various data points utilized in the underwriting, loan and payment processes for financial services within a web portal, integrate with third party applications to apply payments to loans within a web portal, import and store data from third party vendors within a web portal and allow for batch upload of payments. The system can be implemented with the user creating an account or using the system a guest user.

This process can include internal and external individuals and machines for performing inspections (e.g., verifications) . For example, the system can receive a set of internal inspection information entered into the system from an internal inspector representing an internal physical inspection of the project, material or assembly. As the items travel, an internal inspector can provide inspection information representing the stages of the project. The system can also receive a set of external inspection information from an external inspector and an external inspection computer device representing a third-party physical inspection of the project at predetermined stages of the project. Based upon the internal inspection, external inspection or both, an inspection record can be created and stored on the persistent storage.

What is claimed is:

1. A computerized system for verification and management of transactions comprising:
   a kiosk having a controller disposed at a transaction origination location and in communication with a storage system;
   a sensor assembly included in the kiosk and in communications with the controller wherein the sensor assembly is adapted for sensing a user identification information, a transaction request, and a transaction location wherein the transaction request is taken from the group consisting of check cashing, loan asset distribution, asset transfer, and a combination thereof;
   a set of computer readable instructions included in controller adapted for:
      receiving, according to the sensor, the user identification information wherein the user identification includes a user location, an identification date and an identification time and the user identification information is taken from the group consisting of a user image, a user facial attribute, a voice information, a retinal scan, a fingerprint, a venous pattern, a gait information, a handprint, genetic marker, and any combination thereof,
      receiving the transaction request wherein the transaction request includes a transaction request date and a transaction request time,
      determining the transaction origination location,
      determining a kiosk location,
      retrieving an approval criterion from a computer readable medium in communications with the controller,
      comparing the approval criterion with the user identification information and the transaction request,
      initiating a transaction approval wherein the transaction approval includes an approval location, an approval date, and an approval time and when (a) the user identification information and the transaction request are consistent with the approval criterion, (b) when the transaction location, the kiosk location and the user location information are consistent, and (c) when the identification date, the identification time, the request date, and request time are consistent, and,
      storing the transaction approval on the storage system.

2. The computerized system of claim 1 wherein the storage system is a persistent storage system.

3. The computerized system of claim 1 wherein the computer readable instructions are adapted for initiating transfer of funds from a first account to a second account according to the transaction approval.

4. The computerized system of claim 3 wherein the computer readable instructions are adapted for receiving a payment information representing a payment into the first account from the user and reducing a balanced due associated with the second account.

5. The computerized system of claim 4 including a receiver included in the kiosk adapted for receiving a physical payment and wherein the computer readable instructions are adapted for associating the payment information with the transaction approval.

6. The computerized system of claim 5 and wherein the computer readable instructions are adapted for storing the payment information on the storage system.

7. The computerized system of claim 4 wherein the computer readable instructions are adapted for associating the payment information with the transaction approval and storing the payment information on the storage system.

8. The computerized system of claim 1 wherein the computer readable instructions are adapted for initiating a transaction approval upon comparison of the user identification information with a user history information.

9. The computerized system of claim 1 wherein the computer readable instructions are adapted for calculating a chain value according to the transaction approval and an interest rate according to the chain value.

10. The computerized system of claim 1 wherein the computer readable instructions are adapted for receiving an income information from a third party and initiating the transaction approval according to the income information.

11. The computerized system of claim 1 wherein the computer readable instructions are adapted for receiving a history information and initiating the transaction approval according to the history information.

12. The computerized system of claim 1 wherein transaction request includes a check information, and the computer readable instructions are adapted for initiating the transaction approval when the check information includes an existing account.

13. The computerized system of claim 1 wherein transaction request includes a collateral information, and the computer readable instructions are adapted for initiating the transaction according to the collateral information.

14. The computerized system of claim 13 including a documents receipt assembly and the computer readable instructions are adapted for receiving an ownership information associated with the collateral information.

15. A computerized system for verification and management of transactions comprising:
    a kiosk having a controller disposed at a transaction origination location and in communication with a persistent storage;
    a sensor assembly included in the kiosk in communications with the controller wherein the sensor assembly is adapted for receiving a user identification information and a transaction supporting material;
    a set of computer readable instructions included in controller adapted for:
        receiving the user identification information wherein the user identification includes a user location, an identification date, and an identification time,
        receiving the transaction request wherein the transaction request includes a transaction request date and a transaction request time,
        determining a kiosk location,
        comparing an approval criterion with the transaction request,
        initiating a transaction approval wherein the transaction approval includes an approval location, an approval date, and an approval time and when (a) the transaction request is consistent with the approval criterion, (b) when the transaction location, the kiosk location and the user location are consistent, and (c) when the identification date, the identification time, the request date, and request time are consistent, and,
        storing the transaction approval on the persistent storage.

16. The computerized system of claim 15 wherein the computer readable instructions are adapted for receiving a payment information representing a payment into a first account and storing the payment information on the persistent storage.

17. The computerized system of claim 16 wherein the payment is a final payment, and the computer readable instructions are adapted for creating a satisfaction information representing that a loan associated with the transaction approval have been satisfied.

18. The computerized system of claim 15 wherein the computer readable instructions can be adapted for receiving collateral information associated with the transaction approval, capturing collateral identifying information with the sensor assembly, creating a collateral record according to the collateral information and associating the collateral information with the transaction approval.

19. The computerized system of claim 18 wherein the computer readable instructions are adapted for automatically encumbering a title associated with the collateral.

20. The computerized system of claim 18 wherein the computer readable instructions are adapted for automatically storing amounts owned associated with the collateral.

21. The computerized system of claim 19 wherein the computer readable instructions are adapted for recording a lien against the title associated with the collateral.

22. The computerized system of claim 19 wherein the computer readable instructions are adapted for storing an encumbrance associated with the collateral information.

23. The computerized system of claim 22 wherein the computer readable instructions are adapted for storing the encumbrance associated with the collateral information against a digital representation of the collateral.

24. The computerized system of claim 22 wherein the computer readable instructions are adapted for storing the encumbrance associated with an individual associated with the collateral.

25. A computerized system for verification and management of transactions comprising:
    a kiosk having a controller and in communication with a persistent storage;
    a sensor assembly included in the kiosk in communications with the controller;
    a set of computer readable instructions included in controller adapted for:
        receiving a user identification information from the sensor assembly wherein the user identification includes a user location, an identification date, and an identification time,
        receiving the transaction request,
        determining a kiosk location,
        comparing an approval criterion with the transaction request,
        initiating a transaction approval wherein the transaction approval includes an approval location, an approval date, and an approval time and when (a) the transaction request is consistent with the approval criterion, (b) when the transaction location and the user location are consistent, and (c) when the identification date, the identification time, the approval date, and approval time are consistent, and,
        storing the transaction approval on the persistent storage.

26. A computerized system for verification and management of transactions comprising:
    a kiosk having a controller and in communication with a persistent storage;
    a sensor assembly included in the kiosk in communications with the controller;

a set of computer readable instructions included in controller adapted for:
- receiving a user identification information from the sensor assembly wherein the user identification includes a user location, an identification date, and an identification time wherein the user location, the identification date, and the identification time are associated with a biometric information included in the user identification information,
- receiving the transaction request,
- determining a transaction request location,
- comparing an approval criterion with the transaction request,
- initiating a transaction approval wherein the transaction approval includes an approval location, an approval date, and an approval time and when (a) the transaction request is consistent with the approval criterion, (b) when the transaction request location and the user location are consistent, and (c) when the identification date, the identification time, the approval date, and approval time are consistent, and,
- storing the transaction approval on the persistent storage.

* * * * *